(12) United States Patent
Sabelle et al.

(10) Patent No.: US 9,439,844 B2
(45) Date of Patent: Sep. 13, 2016

(54) TRI-AROMATIC AZOMETHINE DIRECT DYES COMPRISING AT LEAST ONE UNIT DERIVED FROM RESORCINOL, DYEING COMPOSITION, METHOD AND USE

(71) Applicant: L'OREAL, Paris (FR)

(72) Inventors: Stephane Sabelle, Paris (FR); Madeline Leduc, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/365,228

(22) PCT Filed: Dec. 13, 2012

(86) PCT No.: PCT/EP2012/075388
§ 371 (c)(1),
(2) Date: Jun. 13, 2014

(87) PCT Pub. No.: WO2013/087772
PCT Pub. Date: Jun. 20, 2013

(65) Prior Publication Data
US 2015/0027483 A1    Jan. 29, 2015

Related U.S. Application Data

(60) Provisional application No. 61/585,005, filed on Jan. 10, 2012.

(30) Foreign Application Priority Data

Dec. 13, 2011 (FR) .................................. 11 61580

(51) Int. Cl.
| | |
|---|---|
| A61Q 5/10 | (2006.01) |
| A61K 8/41 | (2006.01) |
| A61Q 5/06 | (2006.01) |
| C09B 55/00 | (2006.01) |
| A61K 8/34 | (2006.01) |
| A61K 8/35 | (2006.01) |
| A61K 8/42 | (2006.01) |

(52) U.S. Cl.
CPC . *A61K 8/41* (2013.01); *A61K 8/34* (2013.01); *A61K 8/35* (2013.01); *A61K 8/411* (2013.01); *A61K 8/42* (2013.01); *A61Q 5/06* (2013.01); *A61Q 5/065* (2013.01); *A61Q 5/10* (2013.01); *C09B 55/009* (2013.01); *A61K 2800/4322* (2013.01); *A61K 2800/88* (2013.01)

(58) Field of Classification Search
CPC .......... A61Q 5/10; A61Q 5/06; A61Q 5/065; A61K 8/411; A61K 2800/88; A61K 2800/4322; C09B 55/009
USPC .......................................................... 8/405
See application file for complete search history.

(56) References Cited

U.S. PATENT DOCUMENTS

| | | |
|---|---|---|
| 3,787,174 A | 1/1974 | Kalopissis et al. |
| 3,792,090 A | 2/1974 | Kalopissis et al. |
| 3,817,699 A | 6/1974 | Kalopissis et al. |
| 3,853,464 A | 12/1974 | Kalopissis et al. |
| 3,867,094 A | 2/1975 | Kalopissis et al. |
| 3,884,625 A | 5/1975 | Kalopissis et al. |
| 3,894,837 A | 7/1975 | Kalopissis et al. |
| 3,905,761 A | 9/1975 | Kalopissis et al. |
| 3,919,265 A | 11/1975 | Bugaut et al. |
| 3,929,404 A | 12/1975 | Kalopissis et al. |
| 3,953,508 A | 4/1976 | Kalopissis et al. |
| 3,972,937 A | 8/1976 | Kalopissis et al. |
| 4,003,699 A | 1/1977 | Rose et al. |
| 4,042,627 A | 8/1977 | Kalopissis et al. |
| 4,054,147 A | 10/1977 | Kalopissis et al. |
| 4,112,229 A | 9/1978 | Kalopissis et al. |
| RE30,199 E | 1/1980 | Rose et al. |

(Continued)

FOREIGN PATENT DOCUMENTS

| | | |
|---|---|---|
| CH | 581996 A5 | 11/1976 |
| DE | 2359399 A1 | 6/1975 |

(Continued)

OTHER PUBLICATIONS

STIC Search Report dated Feb. 2, 2015.*

(Continued)

*Primary Examiner* — Eisa Elhilo
(74) *Attorney, Agent, or Firm* — The Marbury Law Group, PLLC

(57) ABSTRACT

The present invention relates to azomethine-type direct dyes with a tri-aromatic unit having the following formula (I): and their use for coloring keratin fibers, particularly human keratin fibers such as the hair. The invention also relates to a composition for dyeing keratin fibers comprising, in a suitable medium for dyeing, such direct dyes. Another subject of the present invention is a method for dyeing keratin fibers using said dyeing composition. Finally the present invention also relates to precursors for these direct dyes.

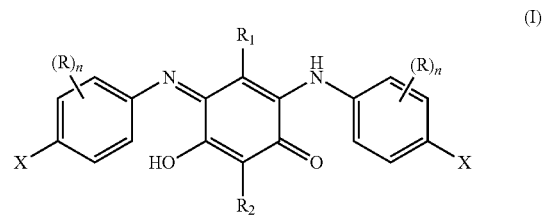

16 Claims, No Drawings

(56) References Cited

U.S. PATENT DOCUMENTS

| | | | |
|---|---|---|---|
| 4,222,958 A | 9/1980 | Kalopissis et al. | |
| 4,260,749 A | 4/1981 | Bugaut et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Mockli | |
| 5,766,576 A | 6/1998 | Lowe et al. | |
| 6,099,592 A | 8/2000 | Vidal et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 8,066,782 B2 | 11/2011 | Leduc et al. | |
| 2002/0050013 A1 | 5/2002 | Vidal et al. | |
| 2003/0019051 A9 | 1/2003 | Vidal et al. | |
| 2004/0194229 A1* | 10/2004 | Lagrange | 8/405 |
| 2011/0041263 A1* | 2/2011 | Leduc et al. | 8/426 |

FOREIGN PATENT DOCUMENTS

| | | | |
|---|---|---|---|
| DE | 3843892 A1 | 6/1990 | |
| DE | 4133957 A1 | 4/1993 | |
| DE | 19543988 A1 | 5/1997 | |
| EP | 0714954 A2 | 6/1996 | |
| EP | 0770375 A1 | 5/1997 | |
| FR | 2047932 | 3/1971 | |
| FR | 2056799 | 5/1971 | |
| FR | 2106661 | 5/1972 | |
| FR | 2121101 | 8/1972 | |
| FR | 2165965 | 8/1973 | |
| FR | 2189380 | 1/1974 | |
| FR | 2234277 | 1/1975 | |
| FR | 2262023 | 9/1975 | |
| FR | 2733749 A1 | 11/1996 | |
| FR | 2801308 A1 | 5/2001 | |
| FR | 2886136 A1 | 12/2006 | |
| FR | 2925049 * | 6/2009 | A61Q 5/10 |
| FR | 2925049 A1 | 6/2009 | |
| GB | 1026978 A | 4/1966 | |
| GB | 1153196 A | 5/1969 | |
| JP | 02019576 | 1/1990 | |
| JP | 05163124 | 6/1993 | |
| WO | 9408969 A1 | 4/1994 | |
| WO | 9408970 A1 | 4/1994 | |
| WO | 9501772 A1 | 1/1995 | |
| WO | 9515144 A1 | 6/1995 | |
| WO | 9615765 A1 | 5/1996 | |
| WO | 2010142777 A1 | 12/2010 | |
| WO | 2013087770 A1 | 6/2013 | |

OTHER PUBLICATIONS

International Search Report for International Application No. PCT/EP2012/075386, published as WO 2013/087770, (Jan. 2013).
International Search Report for International Application No. PCT/EP2012/075388, published as WO 2013/087772, (Mar. 2013).
English language abstract for EP 0770375, (1997).
English language abstract for EP 1728500 (related to FR 2886136), (2006).
English language abstract for JP 02-019576, (1990).
English language abstract for JP 05-163124, (1993).

* cited by examiner

TRI-AROMATIC AZOMETHINE DIRECT DYES COMPRISING AT LEAST ONE UNIT DERIVED FROM RESORCINOL, DYEING COMPOSITION, METHOD AND USE

CROSS REFERENCE TO RELATED APPLICATIONS

This is a national stage application of PCT/EP2012/075388, filed internationally on Dec. 13, 2012, which claims priority to U.S. Provisional Application No. 61/585,005, filed on Jan. 10, 2012, as well as French Application No. 1161580, filed Dec. 13, 2011, all of which are incorporated herein by their entireties.

The present invention relates to specific tri-aromatic azomethine-type direct dyes comprising at least one unit derived from resorcinol and their use for colouring keratin fibres, in particular human keratin fibres such as the hair.

The invention also relates to a composition for dyeing keratin fibres comprising, in a suitable medium for dyeing, such direct dyes and a method for dyeing using said composition.

Lastly, the invention relates to precursors for these direct dyes, their use for colouring fibres and a multi-compartment device containing them.

The present invention relates to the field of dyeing keratin fibres and more particularly to the field of hair dyeing.

It is known practice to dye keratin fibres, and in particular the hair, with dyeing compositions containing one or more direct dyes, according to a "direct dyeing" method.

The method conventionally used in direct dyeing consists in applying to keratin fibres one or more direct dyes, or colouring molecules, which have an affinity for the said fibres, leaving them to take on the fibres, and then rinsing the fibres. The direct dyes used hitherto are generally nitrobenzene dyes, anthraquinone dyes, nitropyridine dyes, dyes of azo, xanthene, acridine or azine type or triarylmethane-based dyes.

These direct dyes may also be applied to keratin fibres in the presence of an oxidizing agent if the goal is to obtain a simultaneous lightening effect for the fibres.

However, the resulting colours are temporary or semi-permanent since the nature of the interactions that bind the direct dyes to the keratin fibre and their desorption from the surface and/or the core of the fibre are responsible for their weak dyeing power and their poor fastness with respect to washing, inclement weather or perspiration.

Moreover, such direct dyes are generally sensitive to the action of oxidizing agents, which makes them difficult to use in particular in lightening direct dye compositions that are formulated from hydrogen peroxide and an alkaline agent, which are similar to compositions used for oxidation dyeing. In other words, direct dyes are generally not very compatible with dyeing compositions intended to lighten fibres and, consequently, using them in a lightening dyeing process as an alternative to oxidation dyeing is not yet entirely satisfactory.

These dyes also have the drawback of lacking light stability, because of the chromophore having low resistance to photochemical attacks, which tends to lead to the colour of the keratin fibres fading over time.

Therefore there is a real need for having direct dyes that not only dye keratin fibres satisfactorily but that are also stable to light, can lead to colours that resist the various attacks that fibres may be subject to, such as inclement weather, washing and perspiration, and further, that are sufficiently stable in the presence of oxidizing agents such as hydrogen peroxide to be able to deliver simultaneous fibre lightening with the benefits set out hereinbefore.

These aims are achieved with the present invention, which particularly relates to azomethine-type direct dyes with a tri-aromatic unit having the following formula (I):

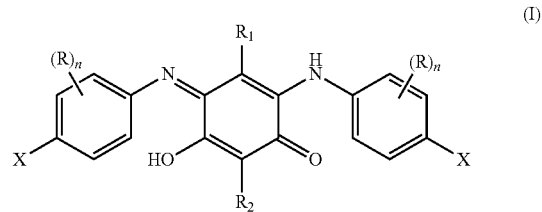

and their organic or inorganic salts with an acid or a base, their tautomeric forms, optical isomers, geometric isomers and/or their solvates;

formula (I) in which:

n denotes an integer equal to 0, 1, 2, 3 or 4;

R denotes:
- a linear or branched $C_1$-$C_4$ alkyl radical, optionally substituted by one or more radicals the same or different chosen from hydroxyl or imidazolium, An$^-$ radicals; An$^-$ designating an anion or a mixture of cosmetically acceptable anions;
- a $C_1$-$C_4$ alkoxy radical;
- a halogen atom;

$R_1$ denotes:
- a hydrogen atom,
- a linear or branched $C_1$-$C_9$ alkyl radical, optionally substituted by one or more hydroxyl radicals,
- a $C_1$-$C_3$ alkoxy radical;

$R_2$ denotes:
- a hydrogen atom,
- a linear or branched $C_3$-$C_9$ alkyl radical, optionally substituted by one or more hydroxyl radicals,
- a $C_1$-$C_3$ alkoxy radicals,
- a $C_1$-$C_2$ alkyl radical when $R_1$ is other than a hydrogen atom;

X denotes:
- a hydroxyl radical,
- a —$NR_3R_4$ radical in which:
  - $R_3$ denotes a hydrogen atom or a linear or branched $C_1$-$C_6$ alkyl radical, optionally substituted by one or more hydroxyl or $C_1$-$C_4$ alkoxy radicals;
  - $R_4$ denotes a hydrogen atom or a linear or branched $C_1$-$C_6$ alkyl radical, optionally substituted by one or more hydroxyl or $C_1$-$C_4$ alkoxy radicals;

it being understood that when $R_1$ and $R_2$ denote a hydrogen atom and n equals 0 then X does not denote a hydroxyl or amino —$NH_2$ radical.

A further subject of the present invention relates to the use of one or more azomethine-type direct dyes of formula (I) as defined previously for colouring keratin fibres, in particular human keratin fibres such as the hair.

The present invention also relates to a composition for dyeing keratin fibres, particularly human keratin fibres such as the hair, comprising, in a suitable medium for dyeing, one or more azomethine-type direct dyes of formula (I) as defined previously.

Specifically, the invention also relates to the use of said dyeing composition for colouring keratin fibres, in particular human keratin fibres such as the hair.

The invention further relates to a colouring method for keratin fibres, particularly human keratin fibres such as the hair, in which said dyeing composition according to the invention is applied to said fibres for a long enough period to obtain the desired colour, after which the fibres are rinsed, optionally washed with shampoo, rinsed again and the resulting fibres are dried or left to dry.

In the same way, the invention relates more specifically to a lightening method for keratin fibres, in particular human keratin fibres such as the hair, in which (i) said dyeing composition free of oxidizing agent and (ii) a cosmetic composition comprising one or more oxidizing agents are applied to said fibres; compositions (i) and (ii) being applied to said keratin fibres sequentially or simultaneously a for long enough period to obtain the desired lightening, after which the fibres are rinsed, optionally washed with shampoo, rinsed again and the resulting fibres are dried or left to dry.

Accordingly, the invention also relates to a multi-compartment device or dyeing kit comprising a first compartment containing one or more direct dyes of formula (I) as defined previously and a second compartment containing one or more oxidizing agents.

The azomethine-type direct dyes of formula (I) according to the invention can thereby lead to colours that resist the various attacks that keratin fibres can be subject to, such as inclement weather, light, washing and perspiration.

What is more, the direct dyes according to the invention can dye keratin fibres satisfactorily, in particular by leading to powerful, chromatic and sparingly selective colours and can lead to an improved uptake colouration.

The direct dyes according to the invention have the benefit of being stable to light and may be used in the presence of an oxidizing agent, which makes using them in lightening direct dye compositions based upon oxidizing agents easier.

In other words, the direct dyes according to the present invention lead to long-lasting colours and are compatible with dyeing compositions that are intended to lighten keratin fibres.

Moreover, the invention relates to leuco-type colourless compounds, which correspond to the reduced form of the azomethine-type direct dyes according to the invention, having the following formula (II):

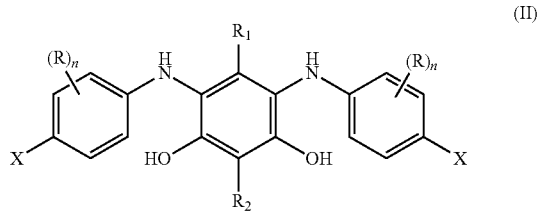

and their organic or inorganic salts with an acid or a base, their tautomeric forms, optical isomers, geometric isomers and/or their solvates such as hydrates;

formula (II) in which n, R, $R_1$, $R_2$ and X have the same meanings as indicated previously.

The leuco-type compounds according to the invention may therefore lead in the presence of one or more oxidizing agents to azomethine-type direct dyes of formula (I).

Accordingly, the invention also relates to the use of one or more leuco-type compounds of formula (II) as precursors for direct dyes of formula (I).

In particular, the invention relates to the use of one or more leuco-type compounds of formula (II) in the presence of one or more oxidizing agents for colouring keratin fibres, in particular human keratin fibres such as the hair.

The invention also relates to a multi-compartment device or dyeing kit containing a first compartment comprising one or more leuco-type compounds of formula (II) such as defined hereinbefore and a second compartment comprising one or more oxidizing agents.

The leuco-type compounds of formula (II) used under oxidizing conditions thereby have the benefit of leading to colours that resist the various attacks that keratin fibres can be subject to, such as inclement weather, washing, light or perspiration.

Other features, aspects, subjects and benefits of the present invention will emerge even more clearly on reading the description and the examples that follow.

I. Azomethine-Type Compound with a Tri-Aromatic Unit

The direct dyes of formula (I) according to the present invention comprise at least one unit derived from resorcinol (meta-dihydroxybenzene) and an azomethine bond.

$An^-$ designates an anion or a mixture of cosmetically acceptable anions such as, for example, halides, such as chloride, methosulfates, nitrates; alkylsulfonates: $Alk-S(O)_2O^-$ such as methylsulfonate or mesylate and ethylsulfonate; arylsulfonates: $Ar-S(O)_2O^-$ such as benzenesulfonate and toluenesulfonate or tosylate; citrate; succinate; tartrate; lactate; alkyl sulfates: $Alk-O-S(O)O^-$ such as methyl sulfate; aryl sulfates such as benzene sulfate and toluene sulfate; phosphate; acetate; triflate; and borates such as tetrafluoroborate.

Preferably, $An^-$ is an anionic counter-ion chosen from bromide, chloride, methyl sulfate, toluenesulfonate ions or a mixture of these ions.

According to one embodiment, in formula (I) for azomethine-type direct dyes according to the invention, considered in isolation or in combination:

n denotes an integer equal to 0, 1 or 2;

R denotes:
- a $C_1$-$C_2$ alkyl radical, optionally substituted by one or more hydroxyl or imidazolium, $An^-$ radicals; $An^-$ designating an anion or a mixture of cosmetically acceptable anions;
- a $C_1$-$C_2$ alkoxy radical;
- a chlorine atom;

$R_1$ denotes:
- a hydrogen atom,
- a linear or branched $C_1$-$C_9$ alkyl radical,
- a linear or branched $C_1$-$C_3$ alkyl radical, substituted by a hydroxyl radical,
- a $C_1$-$C_2$ alkoxy radical;

$R_2$ denotes:
- a hydrogen atom,
- a linear or branched $C_3$-$C_9$ alkyl radical,
- a $C_1$-$C_2$ alkoxy radical,
- a $C_1$-$C_2$ alkyl radical when $R_1$ is other than a hydrogen atom; and/or X denotes:
- a hydroxyl radical,
- a $-NR_3R_4$ radical in which:
  $R_3$ denotes a hydrogen atom or a linear or branched $C_1$-$C_3$ alkyl radical, optionally substituted by one or more hydroxyl or $C_1$-$C_2$ alkoxy radicals;
  $R_4$ denotes a hydrogen atom or a linear or branched $C_1$-$C_3$ alkyl radical, optionally substituted by one or more hydroxyl or $C_1$-$C_2$ alkoxy radicals;

it being understood that when $R_1$ and $R_2$ denote a hydrogen atom and n equals 0 then X does not denote a hydroxyl or amino —$NH_2$ radical.

According to a specific embodiment, in formula (I) for azomethine-type direct dyes according to the invention, considered in isolation or in combination:

n denotes an integer equal to 0, 1 or 2;

R denotes:
- a methyl radical,
- a chlorine atom;

$R_1$ denotes:
- a hydrogen atom,
- a methyl, pentyl or heptyl radical,
- a methyl radical substituted by a hydroxyl radical,
- a methoxy radical;

$R_2$ denotes:
- a hydrogen atom,
- a propyl radical,
- a methoxy radical,
- a methyl radical when $R_1$ is other than a hydrogen atom; and/or X denotes:
- a hydroxyl radical,
- a —$NR_3R_4$ radical in which:
  - $R_3$ denotes a hydrogen atom or an ethyl or isopropyl radical,
  - $R_4$ denotes a hydrogen atom or a linear or branched $C_1$-$C_3$ alkyl radical, optionally substituted by one or more hydroxyl radicals;

it being understood that when $R_1$ and $R_2$ denote a hydrogen atom and n equals 0 then X does not denote a hydroxyl or amino —$NH_2$ radical.

Preferably, n denotes an integer equal to 0, 1 or 2, in particular 1 or 2. Preferably, n denotes an integer equal to 1.

Preferably, R denotes a linear or branched $C_1$-$C_4$ alkyl radical, in particular a $C_1$-$C_2$ alkyl radical. In particular, R denotes a methyl radical.

Preferably, $R_1$ denotes a hydrogen atom or a linear or branched $C_1$-$C_9$ alkyl radical. In particular, R denotes a hydrogen atom or a methyl radical.

In accordance with formula (I) for direct dyes according to the invention, $R_2$ denotes a $C_1$-$C_2$ alkyl radical when $R_1$ is other than a hydrogen atom. In other words, when $R_1$ denotes a hydrogen atom then $R_2$ is other than a $C_1$-$C_2$ alkyl radical.

Preferably, $R_2$ denotes a hydrogen atom.

According to one embodiment, $R_1$ denotes a hydrogen atom or a linear or branched $C_1$-$C_9$ alkyl radical, in particular a $C_1$ alkyl radical, and $R_2$ denotes a hydrogen atom.

According to another embodiment, $R_1$ denotes a hydrogen atom and $R_2$ denotes a $C_1$-$C_2$ alkoxy radical.

According to another embodiment, $R_1$ denotes a linear or branched $C_1$-$C_3$ alkyl radical, substituted by a hydroxyl radical and $R_2$ denotes a hydrogen atom.

According to another embodiment, $R_1$ denotes a hydrogen atom and $R_2$ denotes a linear or branched $C_3$-$C_9$ alkyl radical, in particular a $C_3$ alkyl radical.

According to another embodiment, $R_1$ denotes a linear or branched $C_1$-$C_9$ alkyl radical, in particular $C_1$, and $R_2$ denotes a $C_1$-$C_2$ alkyl radical, in particular a $C_1$ alkyl radical.

Preferably, X denotes a —$NR_3R_4$ radical in which $R_3$ denotes a hydrogen atom or a linear or branched $C_1$-$C_3$ alkyl radical, optionally substituted by a hydroxyl radical and $R_4$ denotes a hydrogen atom or a linear or branched $C_1$-$C_3$ alkyl radical, optionally substituted by a hydroxyl radical.

According to a preferred embodiment, X denotes a —$NR_3R_4$ radical in which $R_3$ and $R_4$ represent a hydrogen atom.

According to another preferred embodiment, X denotes a —$NR_3R_4$ radical in which $R_3$ and $R_4$ are different from a hydrogen atom.

Preferably, the azomethine-type direct dyes of formula (I) according to the invention are chosen from the following compounds and their geometric or optical isomeric forms, their salts with an organic or inorganic acid, or their solvates such as hydrates:

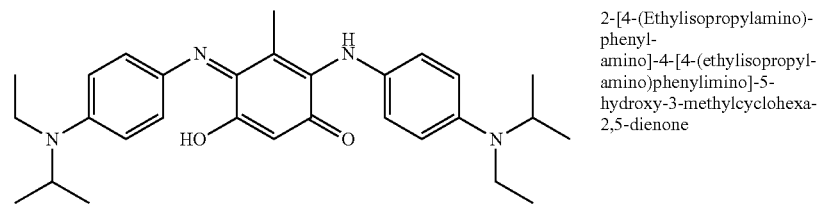

2-[4-(Ethylisopropylamino)-phenyl-amino]-4-[4-(ethylisopropyl-amino)phenylimino]-5-hydroxy-3-methylcyclohexa-2,5-dienone Compound 1

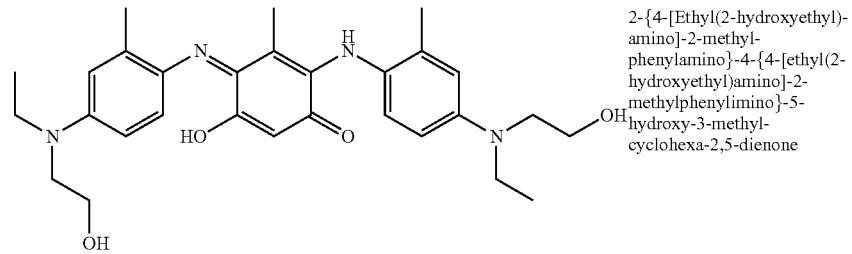

2-{4-[Ethyl(2-hydroxyethyl)-amino]-2-methyl-phenylamino}-4-{4-[ethyl(2-hydroxyethyl)amino]-2-methylphenylimino}-5-hydroxy-3-methyl-cyclohexa-2,5-dienone Compound 2

-continued

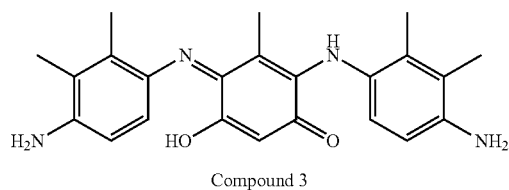 [SMILES: CC1=C(Nc2ccc(N)c(C)c2C)C(=O)C=C(O)/C1=N\c1ccc(N)c(C)c1C]

Compound 3

2-(4-Amino-2,3-dimethyl-phenylamino)-4-[4-amino-2,3-dimethylphenylimino]-5-hydroxy-3-methylcyclohexa-2,5-dienone

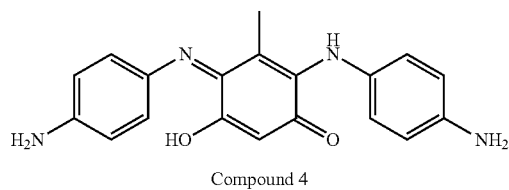 [SMILES: CC1=C(Nc2ccc(N)cc2)C(=O)C=C(O)/C1=N\c1ccc(N)cc1]

Compound 4

2-(4-Aminophenylamino)-4-[4-aminophenylimino]-5-hydroxy-3-methyl-cyclohexa-2,5-dienone

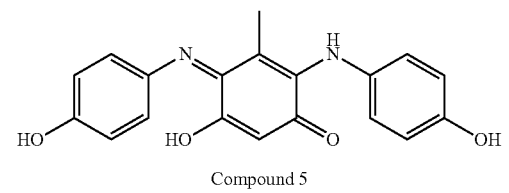 [SMILES: CC1=C(Nc2ccc(O)cc2)C(=O)C=C(O)/C1=N\c1ccc(O)cc1]

Compound 5

5-Hydroxy-2-(4-hydroxy-phenylamino)-4-[4-hydroxyphenylimino]-3-methylcyclohcxa-2,5-dienone

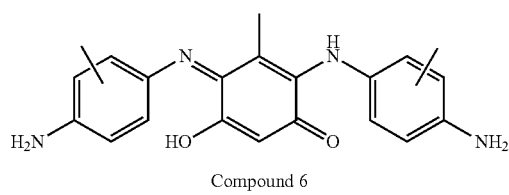

Compound 6

2-(4-Amino-3 (or 2)-methyl-phenylamino)-4-[4-amino-3 (or 2)-methyl-phenylimino]-5-hydroxy-3-methyl-cyclohexa-2,5-dienone

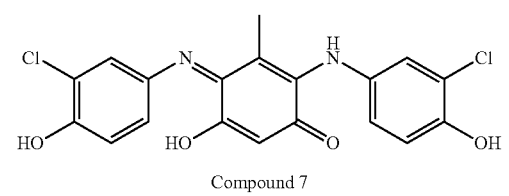 [SMILES: CC1=C(Nc2ccc(O)c(Cl)c2)C(=O)C=C(O)/C1=N\c1ccc(O)c(Cl)c1]

Compound 7

2-(3-Chloro-4-hydroxy-phenylamino)-4-[3-chloro-4-hydroxy-phenylimino]-5-hydroxy-3-methylcyclohexa-2,5-dienone

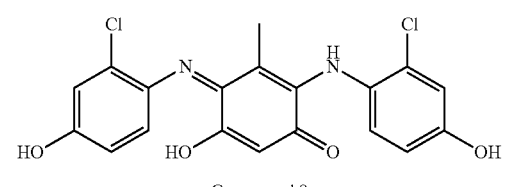

Compound 8

2-(2-Chloro-4-hydroxy-phenylamino)-4-[2-chloro-4-hydroxy-phenylimino]-5-hydroxy-3-methylcyclohexa-2,5-dienone

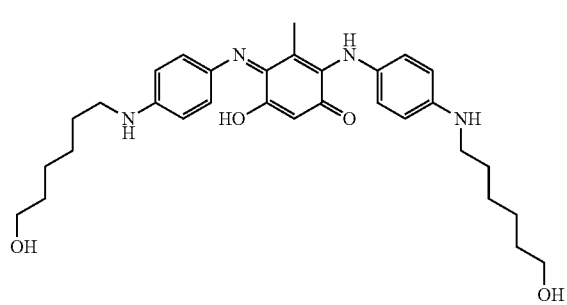

Compound 9

5-Hydroxy-2-[4-(6-hydroxy-hexylamino)phenylamino]-4-[4-(6-hydroxy-hexylamino)phenylimino]-3-methyl-cyclohexa-2,5-dienone -continued

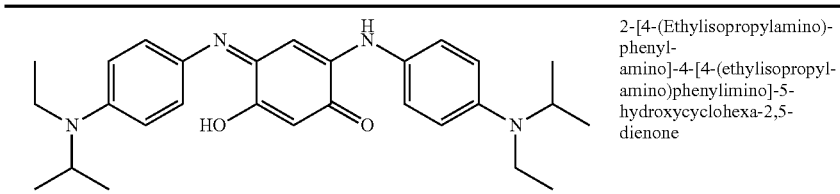

2-[4-(Ethylisopropylamino)-
phenyl-
amino]-4-[4-(ethylisopropyl-
amino)phenylimino]-5-
hydroxycyclohexa-2,5-
dienone Compound 10

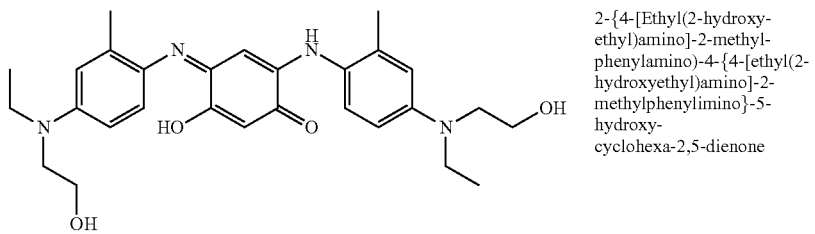

2-{4-[Ethyl(2-hydroxy-
ethyl)amino]-2-methyl-
phenylamino)-4-{4-[ethyl(2-
hydroxyethyl)amino]-2-
methylphenylimino}-5-
hydroxy-
cyclohexa-2,5-dienone Compound 11

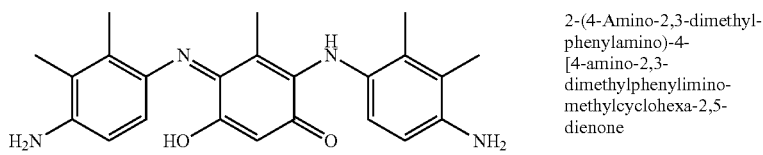

2-(4-Amino-2,3-dimethyl-
phenylamino)-4-
[4-amino-2,3-
dimethylphenylimino-
methylcyclohexa-2,5-
dienone Compound 12

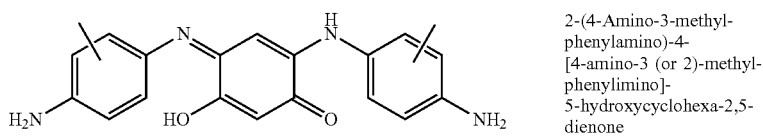

2-(4-Amino-3-methyl-
phenylamino)-4-
[4-amino-3 (or 2)-methyl-
phenylimino]-
5-hydroxycyclohexa-2,5-
dienone Compound 13

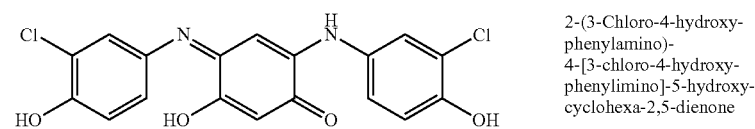

2-(3-Chloro-4-hydroxy-
phenylamino)-
4-[3-chloro-4-hydroxy-
phenylimino]-5-hydroxy-
cyclohexa-2,5-dienone Compound 14

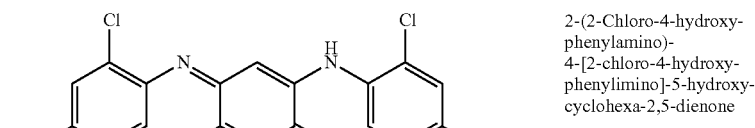

2-(2-Chloro-4-hydroxy-
phenylamino)-
4-[2-chloro-4-hydroxy-
phenylimino]-5-hydroxy-
cyclohexa-2,5-dienone Compound 15

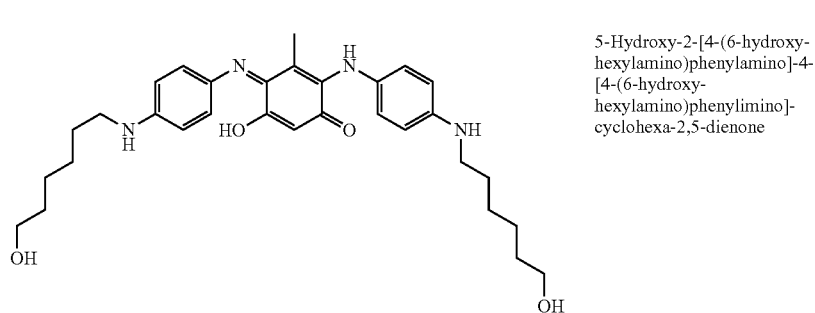

5-Hydroxy-2-[4-(6-hydroxy-
hexylamino)phenylamino]-4-
[4-(6-hydroxy-
hexylamino)phenylimino]-
cyclohexa-2,5-dienone Compound 16

-continued

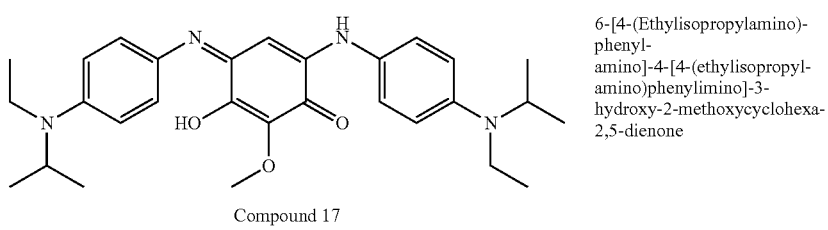

6-[4-(Ethylisopropylamino)-phenyl-amino]-4-[4-(ethylisopropyl-amino)phenylimino]-3-hydroxy-2-methoxycyclohexa-2,5-dienone Compound 17

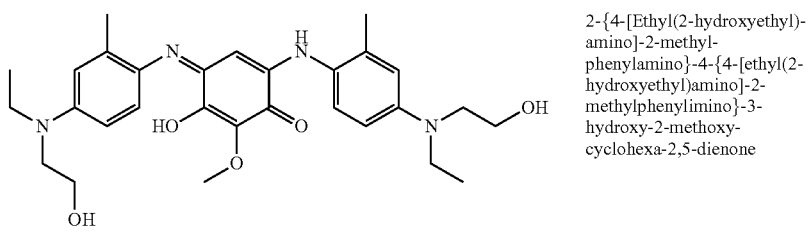

2-{4-[Ethyl(2-hydroxyethyl)-amino]-2-methyl-phenylamino}-4-{4-[ethyl(2-hydroxyethyl)amino]-2-methylphenylimino}-3-hydroxy-2-methoxy-cyclohexa-2,5-dienone Compound 18

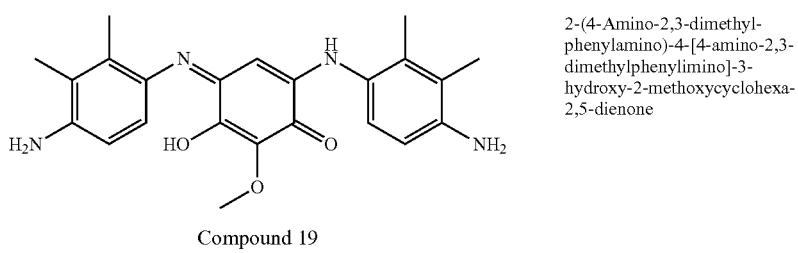

2-(4-Amino-2,3-dimethyl-phenylamino)-4-[4-amino-2,3-dimethylphenylimino]-3-hydroxy-2-methoxycyclohexa-2,5-dienone Compound 19

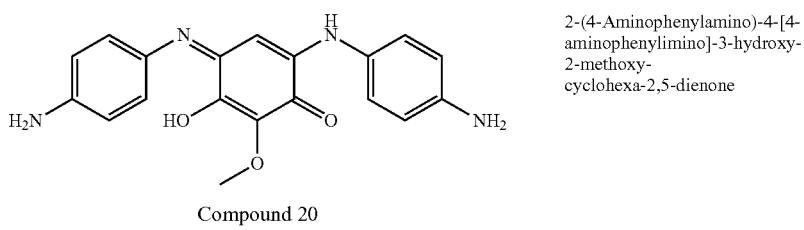

2-(4-Aminophenylamino)-4-[4-aminophenylimino]-3-hydroxy-2-methoxy-cyclohexa-2,5-dienone Compound 20

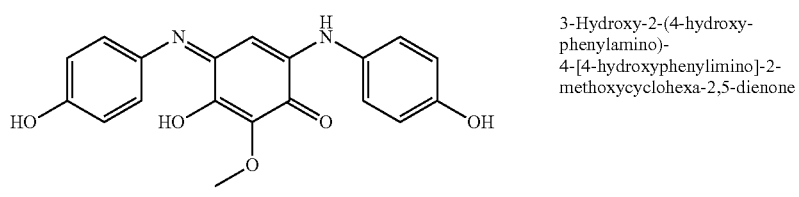

3-Hydroxy-2-(4-hydroxy-phenylamino)-4-[4-hydroxyphenylimino]-2-methoxycyclohexa-2,5-dienone Compound 21

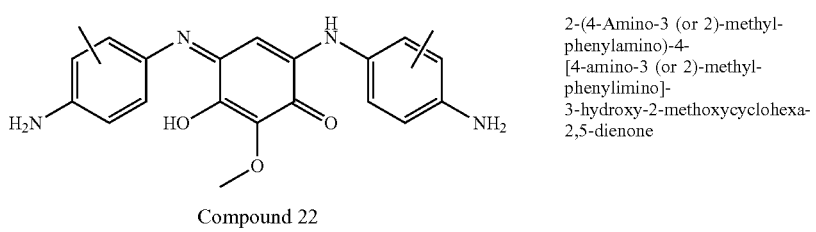

2-(4-Amino-3 (or 2)-methyl-phenylamino)-4-[4-amino-3 (or 2)-methyl-phenylimino]-3-hydroxy-2-methoxycyclohexa-2,5-dienone Compound 22

-continued

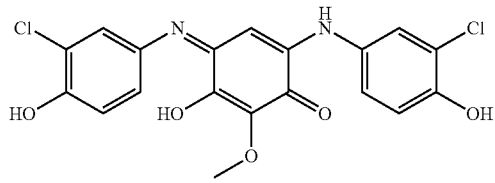

Compound 23

2-(3-Chloro-4-hydroxy-phenylamino)-4-[3-chloro-4-hydroxy-phenylimino]-3-hydroxy-2-methoxycyclohexa-2,5-dienone

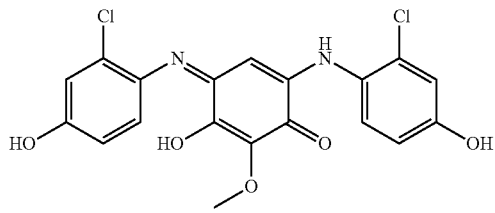

Compound 24

2-(2-Chloro-4-hydroxy-phenylamino)-4-[2-chloro-4-hydroxy-phenylimino]-3-hydroxy-2-methoxycyclohexa-2,5-dienone

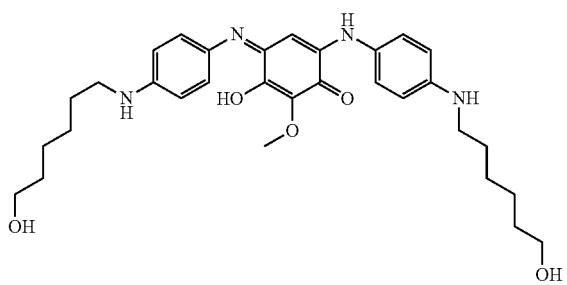

Compound 25

3-Hydroxy-2-[4-(6-hydroxy-hexylamino)phenylamino]-4-[4-(6-hydroxy-hexylamino)phenylimino]-2-methoxy-cyclohexa-2,5-dienone

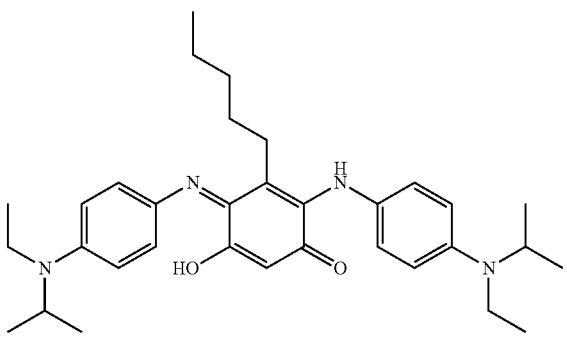

Compound 26

2-[4-(Ethylisopropylamino)-phenyl-amino]-4-[4-(ethylisopropyl-amino)phenylimino]-5-hydroxy-3-pentylcyclohexa-2,5-dienone

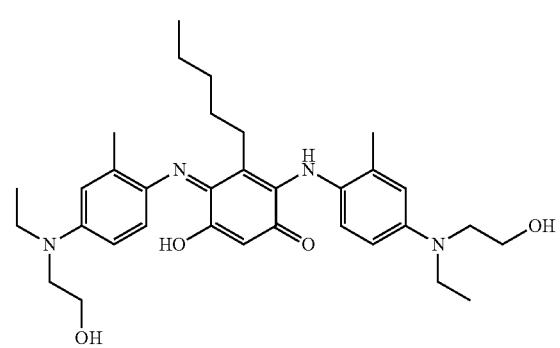

Compound 27

2-{4-[Ethyl(2-hydroxyethyl)-amino]-2-methyl-phenylamino)-4-{4-[ethyl(2-hydroxyethyl)amino]-2-methylphenylimino}-5-hydroxy-3-pentyl-cyclohexa-2,5-dienone -continued

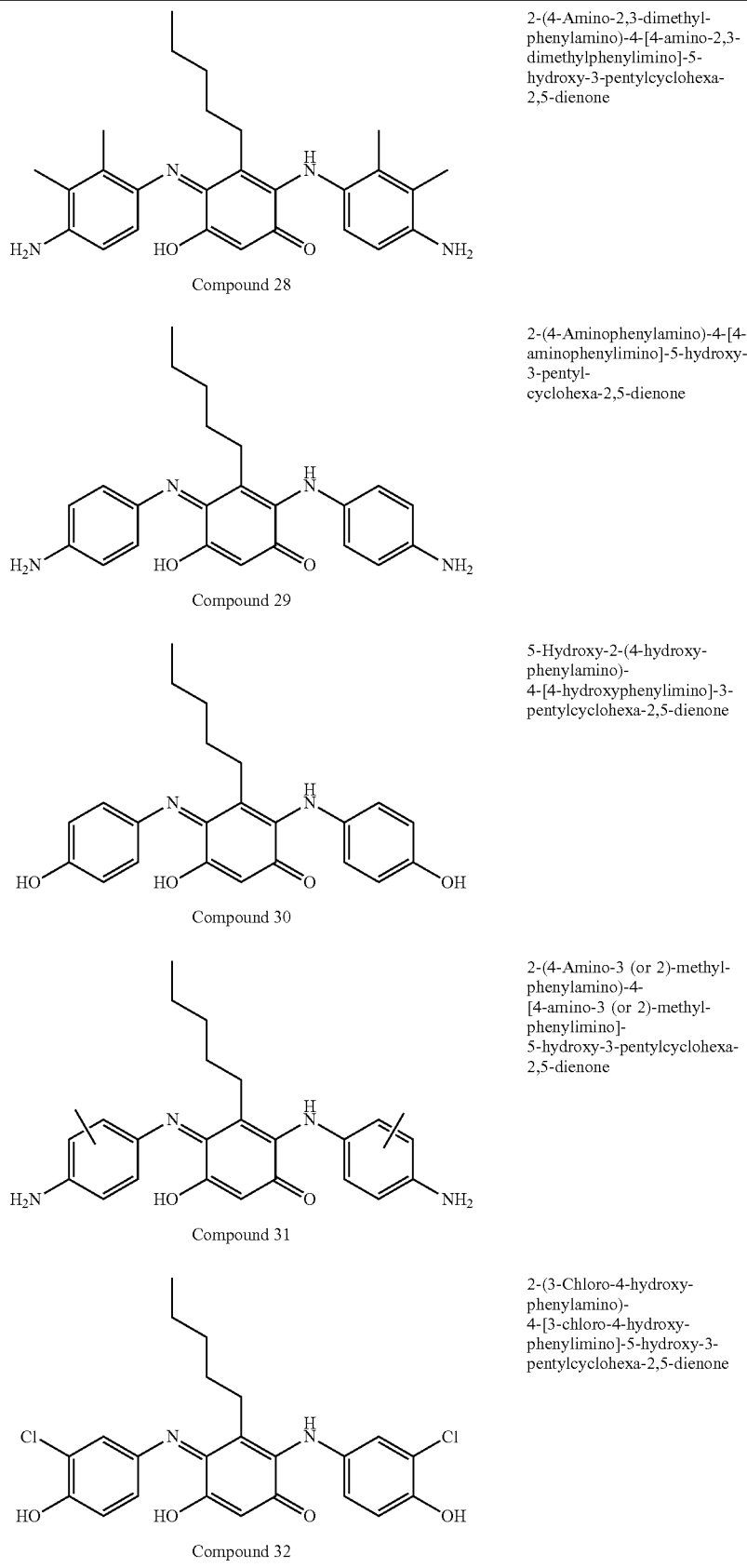

Compound 28: 2-(4-Amino-2,3-dimethyl-phenylamino)-4-[4-amino-2,3-dimethylphenylimino]-5-hydroxy-3-pentylcyclohexa-2,5-dienone Compound 29: 2-(4-Aminophenylamino)-4-[4-aminophenylimino]-5-hydroxy-3-pentyl-cyclohexa-2,5-dienone Compound 30: 5-Hydroxy-2-(4-hydroxy-phenylamino)-4-[4-hydroxyphenylimino]-3-pentylcyclohexa-2,5-dienone Compound 31: 2-(4-Amino-3 (or 2)-methyl-phenylamino)-4-[4-amino-3 (or 2)-methyl-phenylimino]-5-hydroxy-3-pentylcyclohexa-2,5-dienone Compound 32: 2-(3-Chloro-4-hydroxy-phenylamino)-4-[3-chloro-4-hydroxy-phenylimino]-5-hydroxy-3-pentylcyclohexa-2,5-dienone -continued

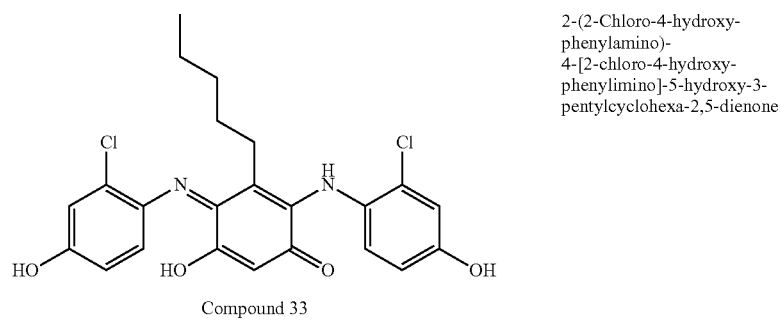

Compound 33

2-(2-Chloro-4-hydroxy-phenylamino)-4-[2-chloro-4-hydroxy-phenylimino]-5-hydroxy-3-pentylcyclohexa-2,5-dienone

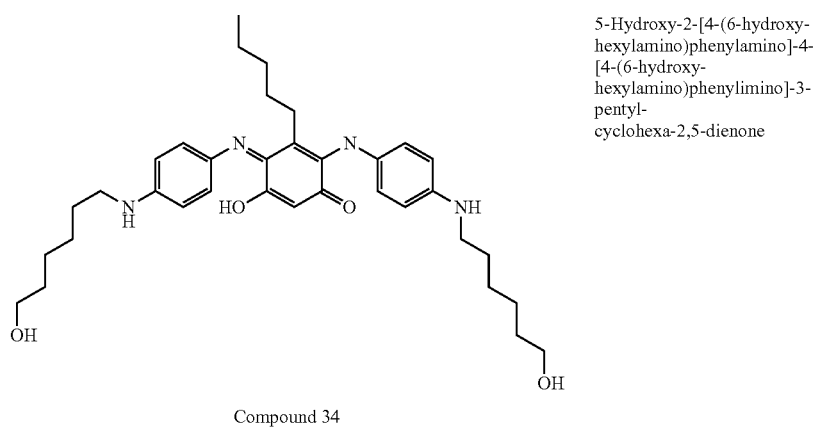

Compound 34

5-Hydroxy-2-[4-(6-hydroxy-hexylamino)phenylamino]-4-[4-(6-hydroxy-hexylamino)phenylimino]-3-pentyl-cyclohexa-2,5-dienone

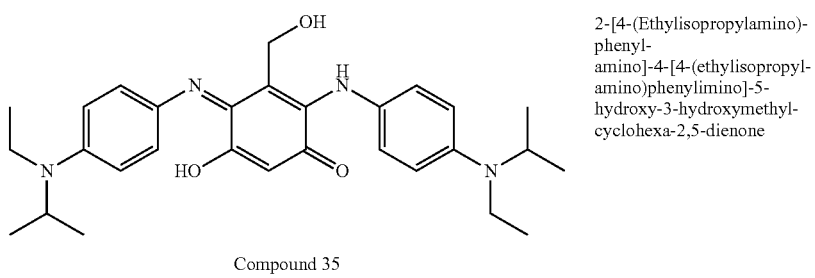

Compound 35

2-[4-(Ethylisopropylamino)-phenyl-amino]-4-[4-(ethylisopropyl-amino)phenylimino]-5-hydroxy-3-hydroxymethyl-cyclohexa-2,5-dienone

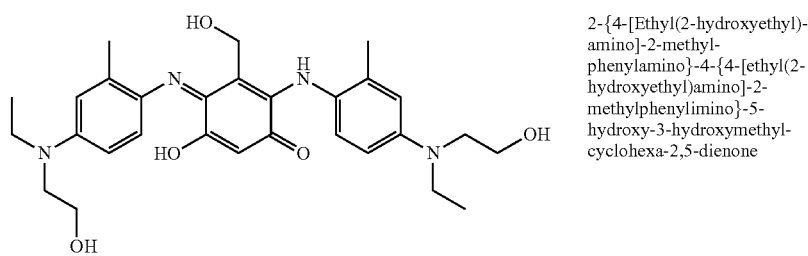

Compound 36

2-{4-[Ethyl(2-hydroxyethyl)-amino]-2-methyl-phenylamino}-4-{4-[ethyl(2-hydroxyethyl)amino]-2-methylphenylimino}-5-hydroxy-3-hydroxymethyl-cyclohexa-2,5-dienone

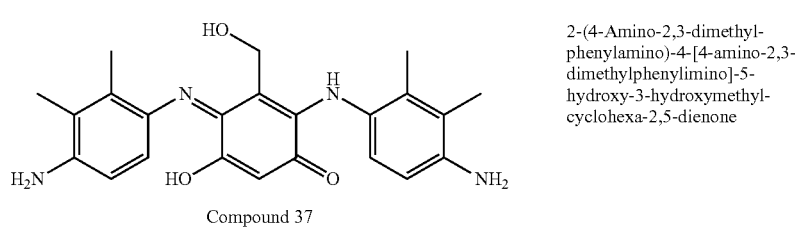

Compound 37

2-(4-Amino-2,3-dimethyl-phenylamino)-4-[4-amino-2,3-dimethylphenylimino]-5-hydroxy-3-hydroxymethyl-cyclohexa-2,5-dienone

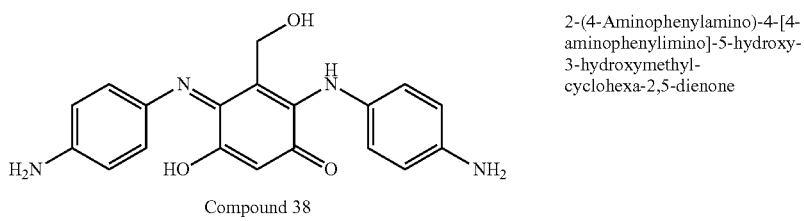

2-(4-Aminophenylamino)-4-[4-aminophenylimino]-5-hydroxy-3-hydroxymethyl-cyclohexa-2,5-dienone Compound 38

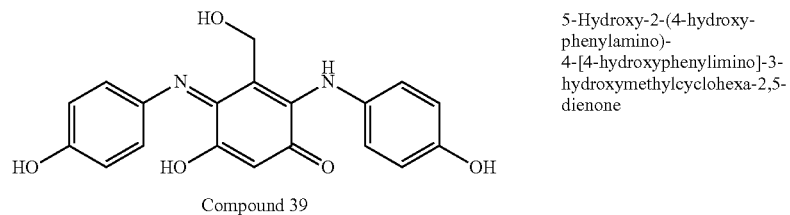

5-Hydroxy-2-(4-hydroxyphenylamino)-4-[4-hydroxyphenylimino]-3-hydroxymethylcyclohexa-2,5-dienone Compound 39

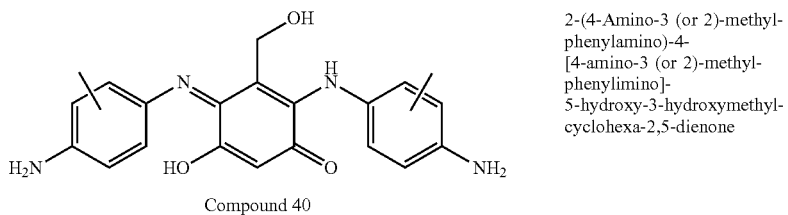

2-(4-Amino-3 (or 2)-methylphenylamino)-4-[4-amino-3 (or 2)-methylphenylimino]-5-hydroxy-3-hydroxymethyl-cyclohexa-2,5-dienone Compound 40

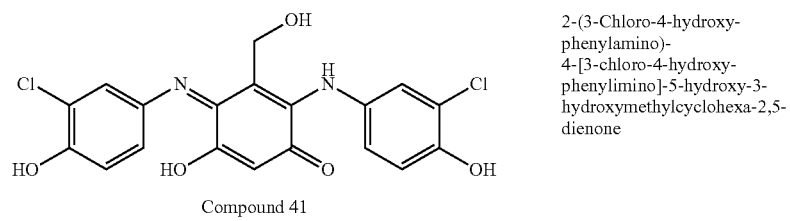

2-(3-Chloro-4-hydroxyphenylamino)-4-[3-chloro-4-hydroxyphenylimino]-5-hydroxy-3-hydroxymethylcyclohexa-2,5-dienone Compound 41

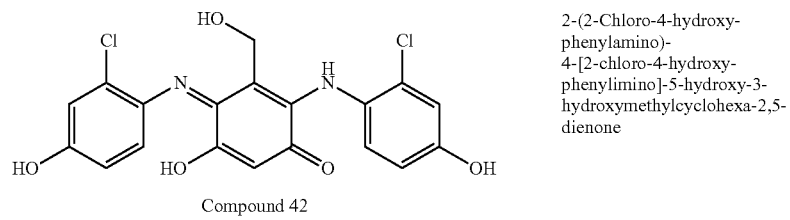

2-(2-Chloro-4-hydroxyphenylamino)-4-[2-chloro-4-hydroxyphenylimino]-5-hydroxy-3-hydroxymethylcyclohexa-2,5-dienone Compound 42

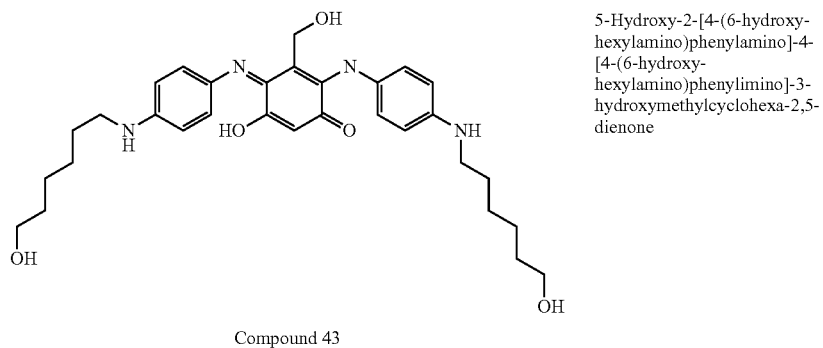

5-Hydroxy-2-[4-(6-hydroxyhexylamino)phenylamino]-4-[4-(6-hydroxyhexylamino)phenylimino]-3-hydroxymethylcyclohexa-2,5-dienone Compound 43

-continued

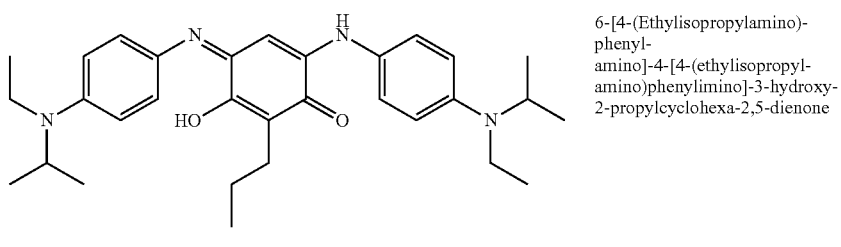

6-[4-(Ethylisopropylamino)-phenyl-amino]-4-[4-(ethylisopropyl-amino)phenylimino]-3-hydroxy-2-propylcyclohexa-2,5-dienone Compound 44

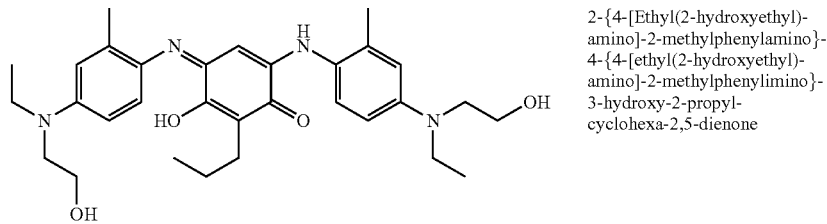

2-{4-[Ethyl(2-hydroxyethyl)-amino]-2-methylphenylamino}-4-{4-[ethyl(2-hydroxyethyl)-amino]-2-methylphenylimino}-3-hydroxy-2-propyl-cyclohexa-2,5-dienone Compound 45

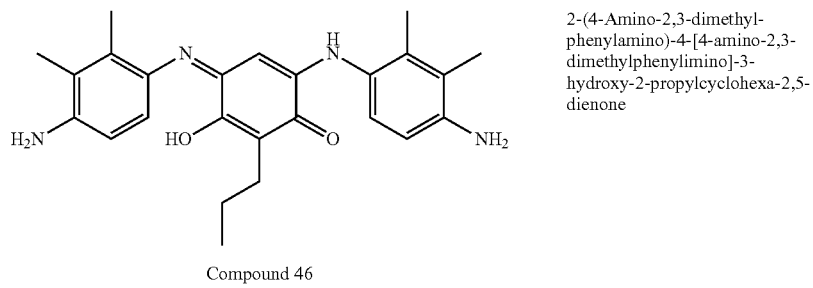

2-(4-Amino-2,3-dimethyl-phenylamino)-4-[4-amino-2,3-dimethylphenylimino]-3-hydroxy-2-propylcyclohexa-2,5-dienone Compound 46

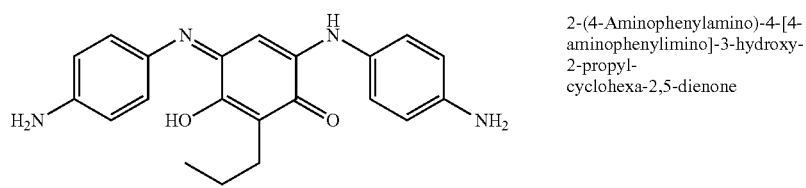

2-(4-Aminophenylamino)-4-[4-aminophenylimino]-3-hydroxy-2-propyl-cyclohexa-2,5-dienone Compound 47

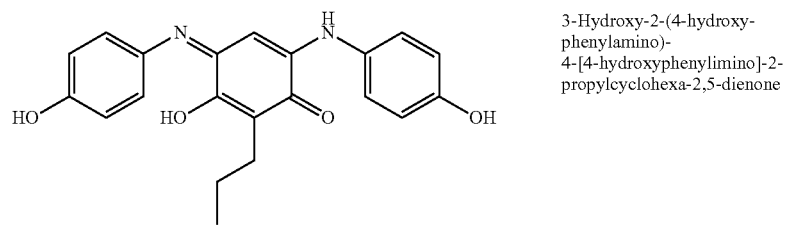

3-Hydroxy-2-(4-hydroxy-phenylamino)-4-[4-hydroxyphenylimino]-2-propylcyclohexa-2,5-dienone Compound 48

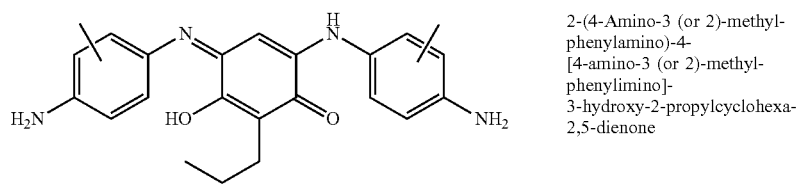

2-(4-Amino-3 (or 2)-methyl-phenylamino)-4-[4-amino-3 (or 2)-methyl-phenylimino]-3-hydroxy-2-propylcyclohexa-2,5-dienone Compound 49

-continued

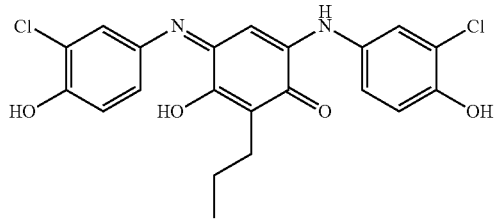

Compound 50

2-(3-Chloro-4-hydroxy-
phenylamino)-
4-[3-chloro-4-hydroxy-
phenylimino]-3-hydroxy-2-
propylcyclohcxa-2,5-dienone

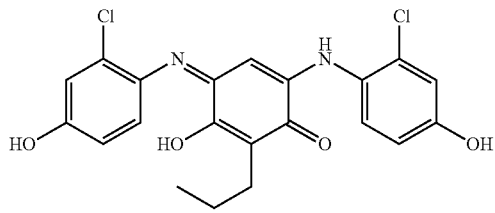

Compound 51

2-(2-Chloro-4-hydroxy-
phenylamino)-
4-[2-chloro-4-hydroxy-
phenylimino]-3-hydroxy-2-
propylcyclohexa-2,5-dienone

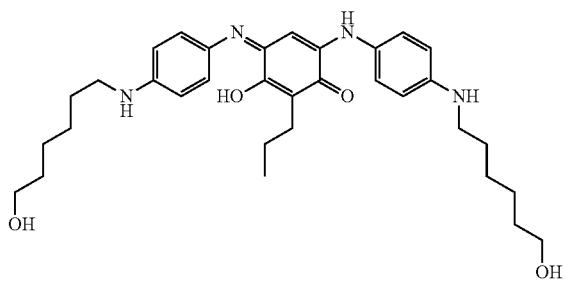

Compound 52

3-Hydroxy-2-[4-(6-hydroxy-
hexylamino)phenylamino]-4-[4-
(6-hydroxy-
hexylamino)phenylimino]-2-
propyl-
cyclohexa-2,5-dienone

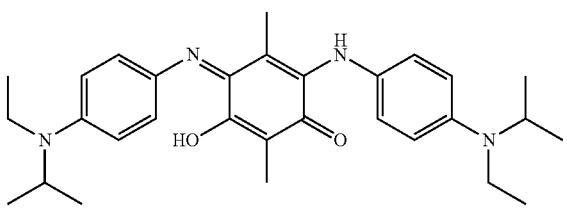

Compound 53

2-[4-(Ethylisopropylamino)-
phenyl-
amino]-4-[4-(ethylisopropyl-
amino)phenylimino]-5-
hydroxy-3,6-dimethyl-
cyclohexa-2,5-dienone

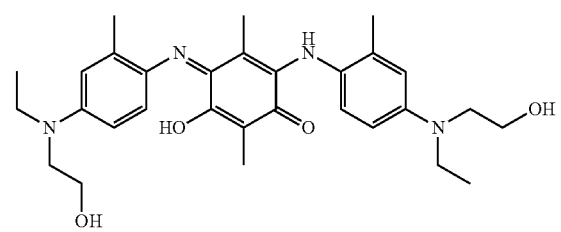

Compound 54

2-{4-[Ethyl(2-hydroxyethyl)-
amino]-2-methyl-
phenylamino}-4-{4-[ethyl(2-
hydroxyethyl)amino]-2-
methylphenylimino}-5-
hydroxy-3,6-dimethyl-
cyclohexa-2,5-dienone

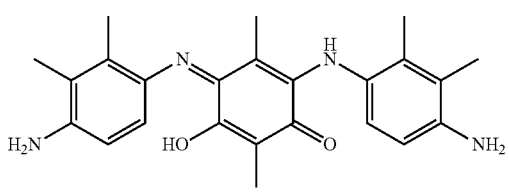

Compound 55

2-(4-Amino-2,3-dimethyl-
phenylamino)-4-[4-amino-2,3-
dimethylphenylimino]-5-
hydroxy-3,6-dimethyl-
cyclohexa-2,5-dienone -continued

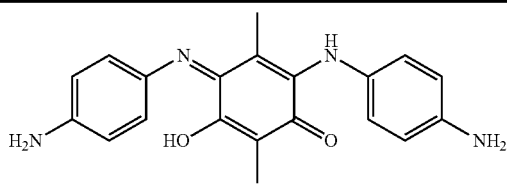

Compound 56

2-(4-Aminophenylamino)-4-[4-aminophenylimino]-5-hydroxy-3,6-dimethylmethyl-cyclohexa-2,5-dienone

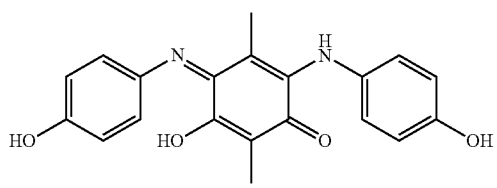

Compound 57

5-Hydroxy-2-(4-hydroxyphenylamino)-4-[4-hydroxyphenylimino]-3,6-dimethylmethyl-cyclohexa-2,5-dienone

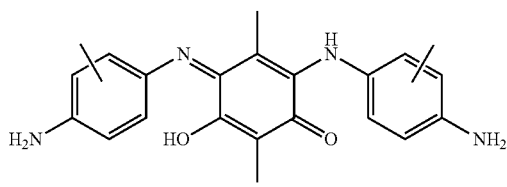

Compound 58

2-(4-Amino-3 (or 2)-methyl-phenylamino)-4-[4-amino-3 (or 2)-methyl-phenylimino]-5-hydroxy-3,6-dimethyl-methylcyclohexa-2,5-dienone

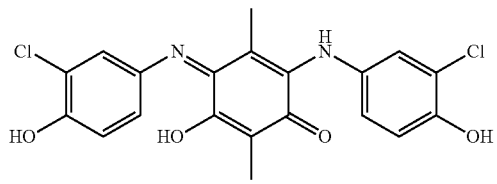

Compound 59

2-(3-Chloro-4-hydroxy-phenylamino)-4-[3-chloro-4-hydroxy-phenylimino]-5-hydroxy-3,6-dimethylmethylcyclohexa-2,5-dienone

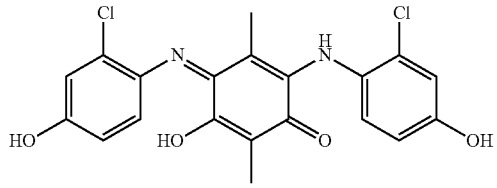

Compound 60

2-(2-Chloro-4-hydroxy-phenylamino)-4-[2-chloro-4-hydroxy-phenylimino]-5-hydroxy-3,6-dimethylmethylcyclohexa-2,5-dienone

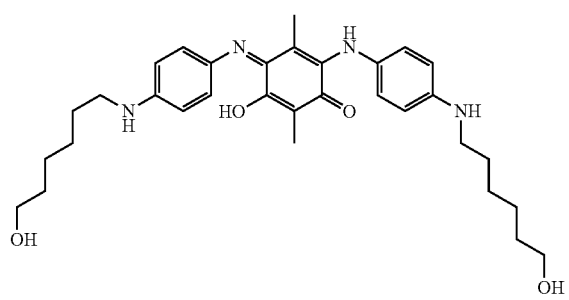

Compound 61

5-Hydroxy-2-[4-(6-hydroxy-hexylamino)phenylamino]-4-[4-(6-hydroxy-hexylamino)phenylimino]-3,6-dimethylmethyl-cyclohexa-2,5-dienone Preferably, the direct dyes of formula (I) according to the present invention are chosen from azomethine-type compounds 1, 2, 3, 12, 13, 17, 19, 26, 28, 35, 37, 44, 46, 53 and 55.

More preferably, the direct dyes of formula (I) are chosen from azomethine-type compounds 1, 2, 3 and 13.

The direct dyes of formula (I) may be obtained according to the procedure described below:

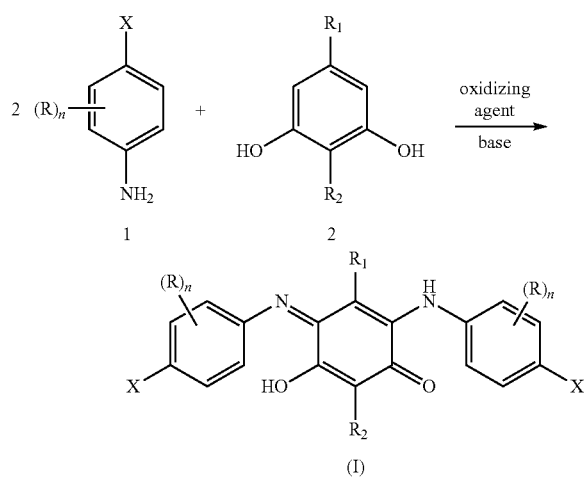

The azomethine-type direct dyes corresponding to formula (I) are generally obtained by reacting two equivalents of derivatives 1 with one equivalent of resorcinol 2 in a basic medium in the presence of an oxidizing agent. The base used is preferably an aqueous solution of ammonia and the oxidizing agent is preferably chosen from hydrogen peroxide, air and ammonium persulfate.

Methods similar to this reaction scheme are described in Patent Applications FR2234277, FR2047932, FR2106661 and FR2121101.

The invention also relates to the use of one or more azomethine-type direct dyes of formula (I) as described previously for colouring keratin fibres, in particular human keratin fibres such as the hair.

II. Dyeing Composition

As indicated hereinbefore, the present invention also relates to a composition for dyeing keratin fibres, particularly human keratin fibres such as the hair, comprising, in a suitable medium for dyeing, one or more direct dyes of formula (I) as defined previously.

Preferably, the dyeing composition comprises one or more direct dyes of formula (I) chosen from azomethine-type compounds 1, 2, 3, 12, 13, 17, 19, 26, 28, 35, 37, 44, 46, 53 and 55 and their mixtures.

More preferably, the dyeing composition comprises one or more direct dyes of formula (I) chosen from azomethine-type compounds 1, 2, 3 and 13 and their mixtures.

The direct dye(s) as defined previously may be present in the dyeing composition according to the invention in a content ranging from 0.001% to 10% by weight, preferably in a content ranging from 0.005% to 6% by weight, relative to the total weight of the dyeing composition.

In accordance with the present invention, the dyeing composition contains one or more direct dyes of formula (I) as defined previously and, optionally, one or more direct dyes having a structure meeting formula (I) defined previously but in which when $R_1$ and $R_2$ denote a hydrogen atom, n equals 0, then X may denote a hydroxyl or amino —$NH_2$ radical.

In other words, the condition defined in formula (I) indicating that when $R_1$ and $R_2$ denote a hydrogen atom, n equals 0 then X does not denote a hydroxyl or amino —$NH_2$ radical does not imply that the dyeing composition according to the invention is free of any azomethine direct dye whose formula (I) would meet the abovementioned condition.

In other words, the abovementioned condition applies only to direct dyes of formula (I) that are necessarily present in the dyeing composition and not those that may be present optionally in said composition.

The dyeing composition according to the invention may further comprise one or more oxidation dyes.

The oxidation dyes are generally chosen from oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and their addition salts.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and their addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and their addition salts with an acid, are particularly preferred.

Mention may be made, among bis(phenyl)alkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and their addition salts.

Mention may be made, among para-aminophenols, by way of example, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol and their addition salts with an acid.

Mention may be made, among ortho-aminophenols, by way of example, of 2-aminophenol, 2-amino-5-methylphenol, 2-amino-6-methylphenol, 5-acetamido-2-aminophenol and their addition salts.

Mention may be made, among heterocyclic bases, by way of example, of pyridine derivatives, pyrimidine derivatives and pyrazole derivatives.

Mention may be made, among pyridine derivatives, of the compounds described, for example, in Patents GB 1 026 978 and GB 1 153 196, such as 2,5-diaminopyridine, 2-(4-methoxyphenyl)amino-3-aminopyridine, 3,4-diaminopyridine and their addition salts.

Other pyridine oxidation bases of use in the present invention are the 3-aminopyrazolo[1,5-a]pyridine oxidation bases or their addition salts described, for example, in Patent Application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a] pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and their addition salts.

Mention may be made, among pyrimidine derivatives, of the compounds described, for example, in Patents DE 2359399, JP 63-169571, JP 05-163124 and EP 0 770 375 or Patent Application WO 96/15765, such as 2,4,5,6-tetraaminopyrimidine, 4-hydroxy-2,5,6-15 triaminopyrimidine, 2-hydroxy-4,5,6-triaminopyrimidine, 2,4dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in Patents DE 3843892, DE 4133957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts. 4,5-Di-amino-1-β-methoxyethyl)pyrazole may also be used.

Use will preferably be made of a 4,5-diaminopyrazole and more preferably still of 4,5-diamino-1-β-hydroxyethyl)pyrazole and/or one of its salts.

Mention may also be made, as pyrazole derivatives, of diamino-N,N-dihydropyrazolopyrazolones and in particular those described in Application FR-A-2 886 136, such as the following compounds and their addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or one of its salts.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or one of their salts.

The dyeing composition may optionally comprise one or more couplers advantageously chosen from those conventionally used in dyeing keratin fibres.

Mention may in particular be made, among these couplers, of meta-phenylenediamines, meta-aminophenols, meta-diphenols, naphthalene couplers, heterocyclic couplers and their addition salts.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a] benzimidazole, their addition salts with an acid, and their mixtures.

In general, the addition salts of the oxidation bases and couplers which can be used in the context of the invention are chosen in particular from the addition salts with an acid, such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight and preferably from 0.005% to 6% by weight relative to the total weight of the composition.

The content of coupler(s), if it is (they are) present, each advantageously represent from 0.001% to 10% by weight relative to the total weight of the composition, and preferably from 0.005% to 6% by weight relative to the total weight of the dyeing composition.

The dyeing composition according to the invention may also comprise one or more additional direct dyes other than the azomethine-type direct dyes defined previously.

The additional direct dye(s) according to the invention are chosen from neutral, acidic or cationic nitrobenzene dyes, neutral, acidic or cationic azo direct dyes, neutral, acidic or cationic quinone and in particular anthraquinone direct dyes, azine direct dyes, triarylmethane direct dyes, azomethine direct dyes and natural direct dyes.

Among the benzene direct dyes that may be used according to the invention, mention may be made, in a non-limiting manner, of the following compounds:
1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-amino ethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene and
1-hydroxy-4-β-hydroxyethylamino-3-nitrobenzene.

Among the azo direct dyes that may be used according to the invention, mention may be made of the cationic azo dyes described in Patent Applications WO 95/15144, WO-95/01772 and EP-714954, the content of which forms an integral part of the invention.

Among these compounds, mention may be made very particularly of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes, described in the Colour Index International, 3rd edition: Disperse Red 17, Acid Yellow 9, Acid Black 1, Basic Red 22, Basic Red 76, Basic Red 51, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
1-N-methylmorpholiniumpropylamino-4-hydroxyanthraquinone
1-aminopropylamino-4-methylamino anthraquinone
1-aminopropylaminoanthraquinone
5-β-hydroxyethyl-1,4-diaminoanthraquinone
2-amino ethylaminoanthraquinone
1,4-bis(β,γ-dihydroxypropylamino)anthraquinone.

Among the azine dyes, mention may be made of the following compounds: Basic Blue 17 and Basic Red 2.

Among the triarylmethane dyes that may be used according to the invention, mention may be made of the following compounds: Basic Green 1, Acid Blue 9, Basic Violet 3, Basic Violet 14, Basic Blue 7, Acid Violet 49, Basic Blue 26 and Acid Blue 7.

Among the azomethine dyes that can be used according to the invention, mention may be made of the following compounds:
2-β-hydroxyethylamino-5-[bis(β-4'-hydroxyethyl)amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinoneimine
3-N-(3'-chloro-4'-methylamino)phenylureido-6-methyl-1,4-benzoquinoneimine
3-[4'-N-(Ethylcarbamylmethyl)amino]phenylureido-6-methyl-1,4-benzoquinoneimine Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and in particular cataplasms or henna-based extracts may also be used.

The additional direct dye(s) may be present in the dyeing composition in a content ranging from 0.001% to 10% by weight, preferably in a content ranging from 0.005% to 6% by weight, relative to the total weight of the composition.

Preferably, the dyeing composition comprises one or more direct dyes of formula (I) such as those defined previously and one or more additional azomethine direct dyes different from the direct dyes of the present invention.

The medium that is suitable for dyeing, also known as the dye support, is a cosmetic medium generally formed from water or a mixture of water and of at least one organic solvent. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and their mixtures.

When they are present, the solvents are present in proportions preferably of between 1% and 99% by weight approximately and even more preferentially between 5% and 95% by weight approximately relative to the total weight of the dyeing composition.

The dyeing composition may also contain various adjuvants conventionally used in hair dye compositions, such as anionic, cationic, non-ionic, amphoteric surfactants or their mixtures, anionic, cationic, non-ionic, amphoteric polymers or their mixtures, inorganic or organic thickeners, and in particular anionic, cationic, non-ionic and amphoteric polymeric associative thickeners, antioxidants, penetrants, sequestrants, solubilizers, fragrances, buffers, dispersants, conditioning agents, for instance volatile or non-volatile, modified or unmodified silicones such as amino silicones, film-forming agents, ceramides, preserving agents, opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the dyeing composition in accordance with the invention are not, or are not substantially, adversely affected by the envisaged addition(s).

The pH of the dyeing composition in accordance with the invention is generally between 3 and 12 approximately, preferably between 5 and 11 approximately and even more particularly from 6 to 8.5. It may be adjusted to the desired value by means of acidifying or alkalinizing agents customarily used in dyeing keratin fibres, or alternatively using standard buffer systems.

Mention may be made, among the acidifying agents, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

Among the alkalinizing agents, mention made be made, by way of example, of aqueous ammonia, alkali metal carbonates, alkanolamines, such as mono-, di- and triethanolamines and their derivatives, sodium hydroxide, potassium hydroxide and the compounds of the following formula (III):

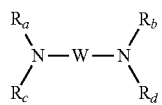

(III)

formula (III) in which W is a propylene residue optionally substituted with a hydroxyl group or a $C_1$-$C_4$ alkyl radical; and $R_a$, $R_b$, $R_c$ and $R_d$, which may be identical or different, denote a hydrogen atom or a $C_1$-$C_4$ alkyl or $C_1$-$C_4$ hydroxyalkyl radical.

The dyeing composition according to the invention may be in various forms, such as in the form of liquids, creams or gels, or in any other form that is suitable for dyeing keratin fibres, and especially human hair.

As indicated previously, the invention also relates to the use of the dyeing composition as defined previously for colouring keratin fibres, in particular human keratin fibres such as the hair.

III. Dyeing Method

The dyeing method according to the present invention consists in applying a dyeing composition as defined previously to keratin fibres for a long enough period to obtain the desired colour, after which the fibres are rinsed, optionally washed with shampoo, rinsed again and the resulting fibres are dried or left to dry.

The dyeing composition is generally applied to keratin fibres at room temperature, preferably between 25 and 55° C.

According to one embodiment, the dyeing composition according to the invention is applied to the keratin fibres in the presence of one or more oxidizing agents for a long enough period to obtain the desired lightening.

The oxidizing agent may be present in the dyeing composition or be used separately in a cosmetic composition.

Preferably, the oxidizing agent is used separately in a cosmetic composition.

Accordingly, the present invention also relates to a lightening method for keratin fibres, in particular human keratin fibres such as the hair, in which (i) the dyeing composition as defined previously free of oxidizing agent and (ii) a cosmetic composition comprising one or more oxidizing agents are applied to said fibres; compositions (i) and (ii) being applied to said keratin fibres sequentially or simultaneously for a long enough period to obtain the desired lightening, after which the fibres are rinsed, optionally washed with shampoo, rinsed again and the resulting fibres are dried or left to dry.

In the sense of the present invention, "sequentially" is understood to mean that the oxidizing composition is applied before or after the dyeing composition, i.e. as a pre- or post-treatment.

The oxidizing agents used are chosen from hydrogen peroxide, urea peroxide, alkali metal bromates, persalts such as perborates and persulfates, peracids and oxidase enzymes (with their optional cofactors), among which mention may be made of peroxidases, 2-electron oxidoreductases such as uricases, and 4-electron oxygenases, for instance laccases.

The oxidizing agent is preferably hydrogen peroxide.

The oxidizing composition may also contain various adjuvants conventionally used in compositions for dyeing the hair and as defined above.

The pH of the oxidizing composition containing the oxidizing agent is such that, after mixing with the dyeing composition, the pH of the resulting composition applied to the keratin fibres preferably ranges between 3 and 12 approximately, more preferably still between 5 and 11, and better still between 6 and 9.5. It may be adjusted to the desired value by means of acidifying or alkalinizing agents usually used in dyeing keratin fibres and as defined above.

V. Leuco-Type Compound

Moreover, the present invention relates to leuco-type compounds having the following formula (II), their organic or inorganic salts with an acid, their tautomeric forms, optical isomers, geometric isomers and/or their solvates:

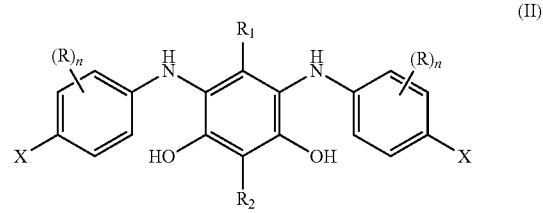

(II)

formula (II) in which n, R, $R_1$, $R_2$ and X have the same meanings as indicated in formula (I).

In particular, the preferred variants for n, R, $R_1$, $R_2$ and X in formula (II) for leuco-type compounds correspond to those indicated in formula (I) for direct dyes.

The leuco-type compounds meeting formula (II) are obtained generally by reacting the azomethine-type compounds of formula (I) with a reducing agent according to the reaction scheme below:

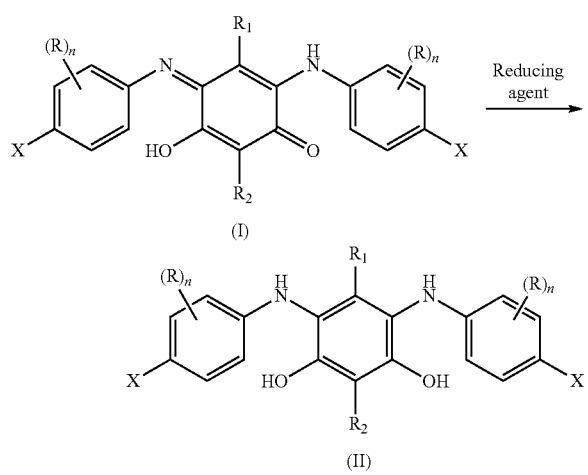

Synthetic processes similar to this reaction scheme are described in Patent Applications FR2056799, FR2047932, FR2165965 and FR2262023.

The leuco-type compounds of formula (II) are used as precursors for direct dyes of formula (I).

Preferably, the leuco-type compounds of formula (II) are chosen from compounds corresponding to the reduced form of azomethine-type direct dyes 1 to 61 mentioned previously.

In other words, the leuco-type compounds of formula (II) are chosen from precursors for azomethine-type direct dyes 1 to 61.

Even more preferably, the leuco-type compounds of formula (II) are chosen from precursors for azomethine direct dyes 1, 2, 3, 12, 13, 17, 19, 26, 28, 35, 37, 44, 46, 53 and 55.

More preferably, the leuco-type compounds of formula (II) are chosen from precursors for direct dyes 1, 2, 3 and 13.

In particular, the invention relates to a cosmetic composition comprising, in a cosmetically acceptable medium, one or more leuco-type compounds of formula (II) as defined previously.

The present invention also relates to a dyeing method in which a cosmetic composition comprising one or more leuco-type compounds of previously cited formula (II) in the presence of one or more oxidizing agents is applied to keratin fibres for a long enough period to develop the desired colour, after which the fibres are rinsed, optionally washed with shampoo, rinsed again and the resulting fibres are dried or left to dry.

The oxidizing agent may be oxygen from the air or be chosen from previously cited oxidizing agents.

In particular, when the oxidizing agent is oxygen from the air, simply exposing the keratin fibres treated with the composition comprising the leuco-type compound(s) to air can generate the colouring species and, consequently, colour the fibres.

According to one variant, the oxidizing agent(s) may be applied to keratin fibres simultaneously or sequentially to the cosmetic composition comprising the leuco-type compounds.

Accordingly, the cosmetic composition comprising the oxidizing agent(s) may be applied to keratin fibres before, simultaneously or after the cosmetic composition comprising the leuco-type compounds of formula (II) according to the invention.

According to another variant, a ready-to-use composition is applied to keratin fibres that results from mixing a cosmetic composition comprising one or more leuco-type compounds having previously cited formula (II) and a cosmetic composition comprising one or more oxidizing agents.

The ready-to-use composition which is ultimately applied to the keratin fibres may be in a variety of forms, such as in the form of liquids, creams or gels or any other form appropriate for carrying out dyeing of keratin fibres, and in particular of human hair.

The leave-on time for the composition(s) varies from 1 to 60 minutes, preferably from 5 to 40 minutes and even more preferably from 10 to 30 minutes.

The cosmetic composition comprising such leuco-type compounds is generally applied to keratin fibres at room temperature, preferably between 25 and 55° C.

Accordingly, the invention relates also to a cosmetic composition, particularly for dyeing human keratin fibres such as the hair, comprising, in a cosmetically acceptable medium, one or more leuco-type compounds of formula (II) as defined previously, optionally in the presence of one or more oxidizing agents.

VI. Dyeing Device

Lastly, the present invention relates to a multi-compartment device or dyeing kit comprising a first compartment containing a cosmetic composition comprising one or more direct dyes having previously cited formula (I) or one or more leuco-type compounds having previously cited formula (II), and optionally a second compartment containing a cosmetic composition comprising one or more oxidizing agents.

The device is suitable for dyeing keratin fibres.

In particular, the invention relates to a multi-compartment device or dyeing kit comprising a first compartment containing a cosmetic composition comprising one or more direct dyes having previously cited formula (I) or one or more leuco-type compounds having previously cited formula (II), and a second compartment containing a cosmetic composition comprising one or more oxidizing agents.

Accordingly, the invention relates to a multi-compartment device or dyeing kit comprising a first compartment containing a cosmetic composition comprising one or more direct dyes having previously cited formula (I) free of oxidizing agent, and a second compartment containing a cosmetic composition comprising one or more oxidizing agents.

Moreover, the invention relates to a multi-compartment device or dyeing kit comprising a first compartment containing a cosmetic composition comprising one or more leuco-type compounds having previously cited formula (II), and a second compartment containing a cosmetic composition comprising one or more oxidizing agents.

According to a specific embodiment, the device comprises at least one compartment containing a cosmetic composition comprising one or more leuco-type compounds having previously cited formula (II).

In this case, the composition comprising the leuco-type compound(s) as defined hereinbefore is applied to keratin fibres that are coloured when they are exposed to air.

The evaluation of the coloration can be done visually or read on a spectrocolorimeter (such as Minolta CM3600d, illuminant D65, angle 10°, SCI values) for the L*, a*, b* colorimetric measurements. In this L*, a*, b* system, L* represents the intensity of the color, a* indicates the green/red color axis and b* indicates the blue/yellow color axis. The lower the value of L, the darker or more intense the color is. The higher the value of a*, the redder the shade is; the higher the value of b*, the yellower the shade is.

The variation in coloring between the colored locks of natural white hair which is untreated (control) and after treatment or coloration is defined by ΔE*, corresponding to the colour uptake on keratin fibers, according to the following equation:

$$\Delta E^* = \sqrt{(L^* - L_0^*)^2 + (a - a_0^*)^2 + (b^* - b_0^*)^2} \quad (i)$$

In this equation, L*, a* and b* represent the values measured after dyeing the natural hair comprising 90% of white hairs and $L_0^*$, $a_0^*$ and $b_0^*$ represent the values measured for the untreated natural hair comprising 90% of white hairs.

The greater the value of ΔE, the greater the difference in color between the control locks and the dyed locks and the greater color uptake is. Chromaticity in the CIE L*, a*, b* colorimetric system is calculated according to the following equation:

$$C^* = \sqrt{a^{*2} + b^{*2}}$$

The greater the value of C*, the greater the chromaticity is.

The examples that follow serve to illustrate the invention without, however, being limiting in nature.

EXAMPLES

I. Examples of Synthesis

Example 1

Synthesis of 2-[4-(ethylisopropylamino)-phenylamino]-4-[4-(ethylisopropylamino)phenylimino]-5-hydroxy-3-methylcyclohexa-2,5-dienone (Compound 1)

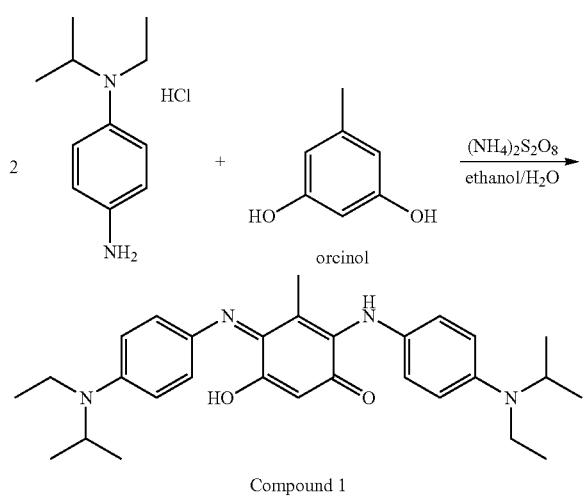

Compound 1

To a solution of 0.002 mol (429 mg) of N-ethyl-N-isopropyl-4-aminoaniline hydrochloride and 0.001 mol (124 mg) of orcinol in 2 ml of water and 6 ml of ethanol brought to a pH of 9.5 with a solution of 20% aqueous ammonia, 0.002 mol (456 mg) of ammonium persulfate dissolved in 1 ml of water is added dropwise. The temperature is held below 30° C. during the addition. At the end of the addition, the precipitate formed is filtered and washed with water.

Thus 125 mg of a black powder corresponding to compound 1 is obtained.

The molecular ion 475 (ES+) is detected by mass.

Example 2

Synthesis of 2-{4-[ethyl(2-hydroxyethyl)-amino]-2-methylphenylamino}-4-{4-[ethyl(2-hydroxyethyl)amino]-2-methylphenylimino}-5-hydroxy-3-methylcyclohexa-2,5-dienone (Compound 2)

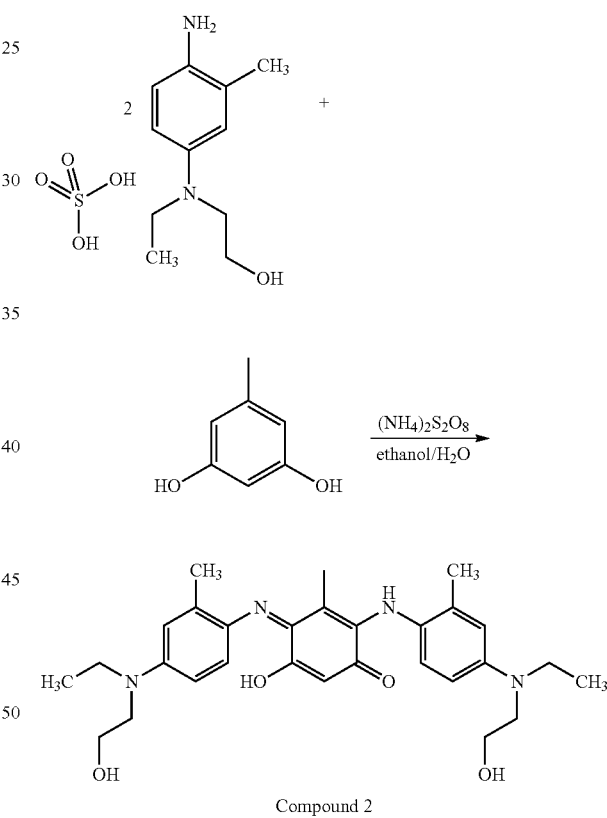

Compound 2

To a solution of 0.002 mol (573 mg) of 2-[(4-amino-3-methylphenyl)ethylamino]ethanol sulfate and 0.001 mol (124 mg) of orcinol in 2 ml of water and 2 ml of ethanol brought to a pH of 9.5 with a solution of 20% aqueous ammonia, 0.002 mol (456 mg) of ammonium persulfate dissolved in 1 ml of water is added dropwise. The temperature is held below 30° C. At the end of the addition, the precipitate formed is filtered and washed with water.

108 mg of a black powder corresponding to compound 2 is obtained.

The molecular ion 507 (ES+) is detected by mass.

Example 3

Synthesis of 2-(4-amino-3 (or 2)-methyl-phenylamino)-4-[4-amino-3 (or 2)-methylphenylimino]-5-hydroxy-cyclohexa-2,5-dienone (Compound 13)

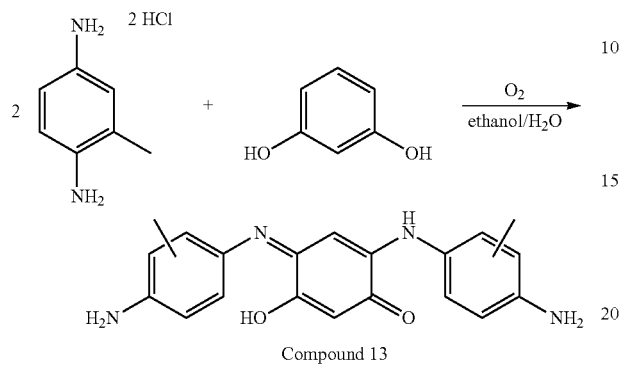

Compound 13

Air at room temperature is bubbled through a solution of 0.2 mol (39 g) of 2-methylbenzene-1,4-diamine dihydrochloride, 0.1 mol (11 g) of resorcinol in 500 ml of water and 50 ml of 20% aqueous ammonia for 4 hours. After the precipitate is filtered, washed with water and then ethanol, 190 mg of a black powder corresponding to compound 13 is obtained.

The molecular ion 349 (ES+) is detected by mass.

Example 4

Synthesis of 2-(4-amino-2,3-dimethyl-phenylamino)-4-[(Z)-4-amino-2,3-dimethylphenylimino]-5-hydroxy-3-methylcyclohexa-2,5-dienone (Compound 3)

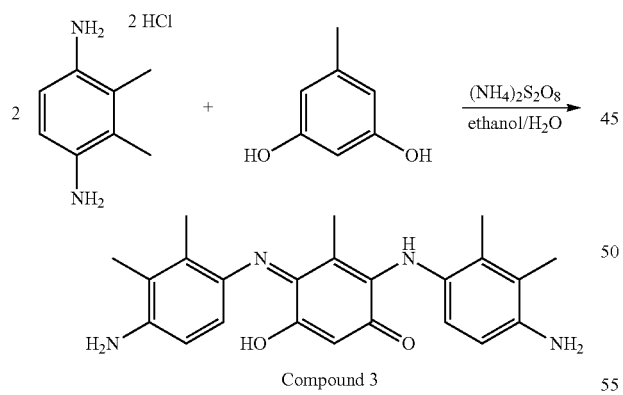

Compound 3

To a solution of 0.02 mol (4.23 g) of 2,3-dimethylbenzene-1,4-diamine dihydrochloride and 0.01 mol (1.24 g) of orcinol in 20 ml of water and 30 ml of ethanol brought to a pH of 9.5 with a solution of 20% aqueous ammonia, 0.01 mol (2.28 g) of ammonium persulfate dissolved in 10 ml of water is added dropwise. The temperature is held below 30° C. At the end of the addition, the precipitate formed is filtered and washed with water.

110 mg of a black powder corresponding to compound 3 is obtained.

The molecular ion 391 (ES+) is detected by mass.

II. Dyeing Evaluations of Compounds Synthesized

The following colouring base is prepared:
- 78.5 grams of water,
- 15 grams of ethanol,
- 5 grams of benzyl alcohol,
- 1.5 gram of oleocetyl dimethyl hydroxyethyl ammonium chloride The pH of the colouring base is adjusted to a value of 9.5 with aqueous ammonia at 20% by weight. 6.25 mg of the dyes described in synthesis examples 1, 2 and 4 are mixed.

Each of the compositions obtained is applied to 0.25 gram tresses of grey hair with 90% whites. After 30 minutes leave-on time, the tress is rinsed, washed with a standard shampoo, then rinsed again and dried.

The results are collated in the following table:

| | |
|---|---|
| Compound 1 | Average orangey grey |
| Compound 2 | Average orangey grey |
| Compound 3 | Dark yellowish beige |

The invention claimed is:

1. An azomethine-type direct dye with a tri-aromatic unit of formula (I), the organic or inorganic acid or base salts thereof, the tautomeric forms thereof, the optical isomers and geometric isomers thereof, and/or the solvates thereof:

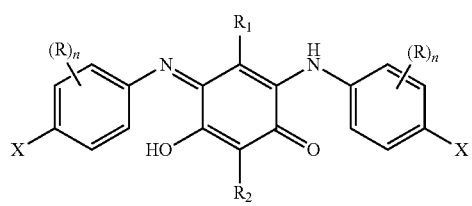

wherein:
n is an integer equal to 0, 1, 2, 3 or 4;
R is chosen from:
  a linear or branched $C_1$-$C_4$ alkyl radical,
  a linear or branched $C_1$-$C_4$ alkyl radical substituted with at least one radical chosen from hydroxyl, imidazolium, and An⁻ radicals, wherein An⁻ represents a cosmetically acceptable anion or a combination of anions,
  a $C_1$-$C_4$ alkoxy radical, and
  a halogen atom;
$R_1$ is chosen from:
  a hydrogen atom,
  a linear or branched $C_1$-$C_9$ alkyl radical,
  a linear or branched $C_1$-$C_9$ alkyl radical substituted with at least one hydroxyl radical, and
  a $C_1$-$C_3$ alkoxy radical;
$R_2$ is chosen from:
  a hydrogen atom, and
  a $C_1$-$C_3$ alkoxy radical;
X is chosen from:
  a hydroxyl radical, and
  a —NR₃R₄ radical wherein $R_3$ is chosen from a hydrogen atom, or a linear or branched $C_1$-$C_6$ alkyl radical, and $R_4$, which may be identical or different, is chosen from a hydrogen atom, a linear or branched $C_1$-$C_6$ alkyl radical, or a linear or branched $C_1$-$C_6$ alkyl radical substituted with at least one hydroxyl or $C_1$-$C_4$ alkoxy radical;

when $R_1$ and $R_2$ represent a hydrogen atom and n equals 0 then X does not represent a hydroxyl or amino —$NH_2$ radical.

2. Azomethine direct dye according to claim 1, wherein:
n is an integer equal to 0, 1 or 2;
R is chosen from:
a $C_1$-$C_2$ alkyl radical,
a $C_1$-$C_2$ alkyl radical substituted with at least one radical chosen from hydroxyl, imidazolium, and $An^-$ radicals; wherein $An^-$ represents a cosmetically acceptable anion or mixture of anions,
a $C_1$-$C_2$ alkoxy radical, and
a chlorine atom;
$R_1$ is chosen from:
a hydrogen atom,
a linear or branched $C_1$-$C_9$ alkyl radical,
a linear or branched $C_1$-$C_3$ alkyl radical substituted with a hydroxyl radical, and
a $C_1$-$C_2$ alkoxy radical;
$R_2$ is chosen from:
a hydrogen atom, and
a $C_1$-$C_2$ alkoxy radical;
X is chosen from:
a hydroxyl radical, and
a —$NR_3R_4$ radical wherein $R_3$ is chosen from a hydrogen atom, or a linear or branched $C_1$-$C_3$ alkyl radical, and $R_4$, which may be identical or different, is chosen from:
a hydrogen atom,
a linear or branched $C_1$-$C_3$ alkyl radical, or
a linear or branched $C_1$-$C_3$ alkyl radical substituted with at least one hydroxyl or $C_1$-$C_2$ alkoxy radical;
when $R_1$ and $R_2$ denote a hydrogen atom and n equals 0 then X does not denote a hydroxyl or amino —$NH_2$ radical.

3. The azomethine direct dye according to claim 1, wherein $R_1$ is chosen from a hydrogen atom and a linear or branched $C_1$-$C_9$ alkyl radical.

4. The azomethine direct dye according to claim 1, wherein $R_2$ is a hydrogen atom.

5. The azomethine direct dye according to claim 1, wherein X is an amino —$NR_3R_4$ radical in which $R_3$ is chosen from a hydrogen atom and a linear or branched $C_1$-$C_3$ alkyl radical, and $R_4$ is chosen from a hydrogen atom and a linear or branched $C_1$-$C_3$ alkyl radical, optionally substituted by a hydroxyl radical.

6. The azomethine direct dye according to claim 1, wherein the compound is chosen from the following compounds and the geometric or optical isomeric forms thereof, the salts with an organic or inorganic acid thereof, and the solvates thereof:

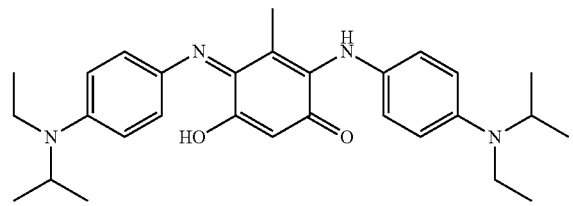

2-[4-(Ethylisopropylamino)-phenyl-amino]-4-[4-(ethylisopropyl-amino)phenylimino]-5-hydroxy-3-methylcyclohexa-2,5-dienone Compound 1

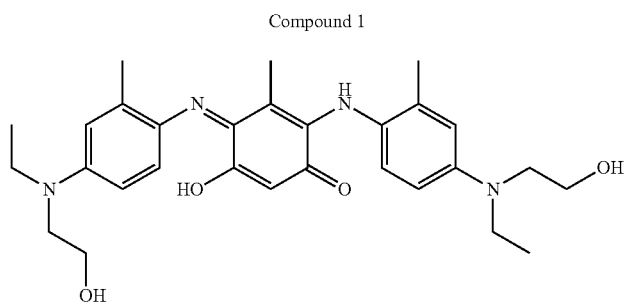

2-{4-[Ethyl(2-hydroxyethyl)-amino]-2-methyl-phenylamino}-4-{4-[ethyl(2-hydroxyethyl)-amino]-2-methylphenylimino}-5-hydroxy-3-methyl-cyclohexa-2,5-dienone Compound 2

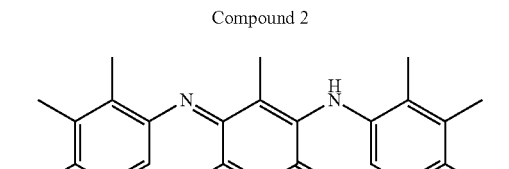

2-(4-Amino-2,3-dimethyl-phenylamino)-4-[4-amino-2,3-dimethylphenylimino]-5-hydroxy-3-methylcyclohexa-2,5-dienone Compound 3

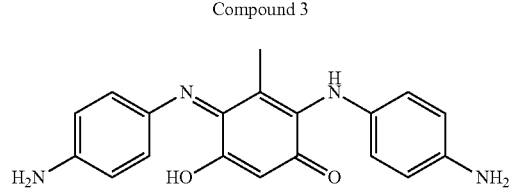

2-(4-Aminophenylamino)-4-[4-aminophenylimino]-5-hydroxy-3-methyl-cyclohexa-2,5-dienone Compound 4

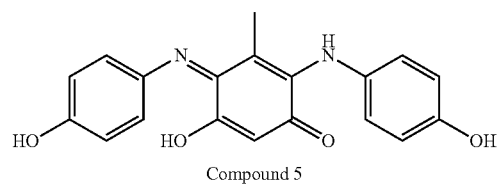 [SMILES: CC1=C(Nc2ccc(O)cc2)C(=O)C=C(O)/C1=N\c1ccc(O)cc1]

5-Hydroxy-2-(4-hydroxyphenylamino)-4-[4-hydroxyphenylimino]-3-methylcyclohexa-2,5-dienone Compound 5

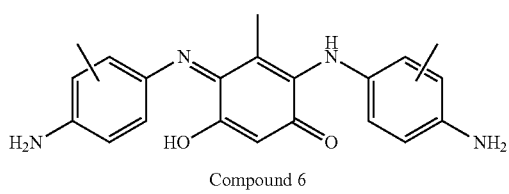

2-(4-Amino-3 (or 2)-methylphenylamino)-4-[4-amino-3 (or 2)-methylphenylimino]-5-hydroxy-3-methylcyclohexa-2,5-dienone Compound 6

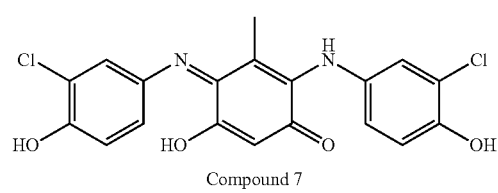 [SMILES: CC1=C(Nc2ccc(O)c(Cl)c2)C(=O)C=C(O)/C1=N\c1ccc(O)c(Cl)c1]

2-(3-Chloro-4-hydroxyphenylamino)-4-[3-chloro-4-hydroxyphenylimino]-5-hydroxy-3-methylcyclohexa-2,5-dienone Compound 7

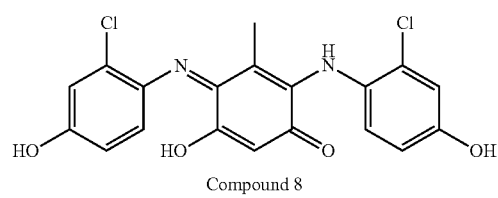 [SMILES: CC1=C(Nc2ccc(O)cc2Cl)C(=O)C=C(O)/C1=N\c1ccc(O)cc1Cl]

2-(2-Chloro-4-hydroxyphenylamino)-4-[2-chloro-4-hydroxyphenylimino]-5-hydroxy-3-methylcyclohexa-2,5-dienone Compound 8

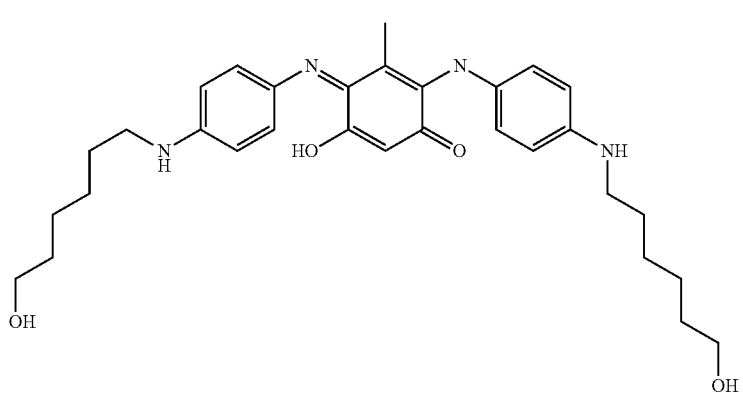

5-Hydroxy-2-[4-(6-hydroxyhexylamino)phenylamino]-4-[4-(6-hydroxyhexylamino)phenylimino]-3-methylcyclohexa-2,5-dienone Compound 9

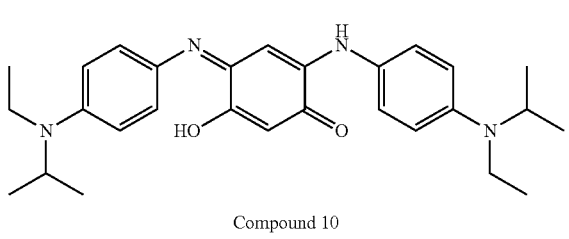 [SMILES: CCN(c1ccc(/N=C2/C=C(Nc3ccc(N(CC)C(C)C)cc3)C(=O)C=C2O)cc1)C(C)C]

2-[4-(Ethylisopropylamino)phenylamino]-4-[4-(ethylisopropylamino)phenylimino]-5-hydroxycyclohexa-2,5-dienone Compound 10

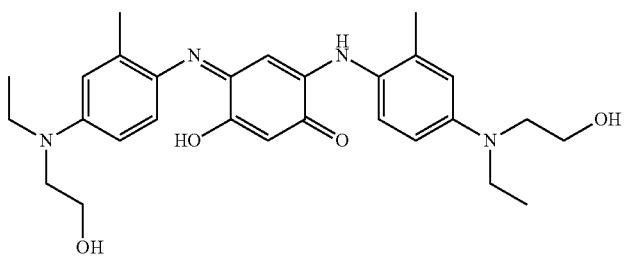

2-{4-[Ethyl(2-hydroxy-ethyl)amino]-2-methyl-phenylamino}-4-{4-[ethyl(2-hydroxyethyl)amino]-2-methylphenylimino}-5-hydroxy-cyclohexa-2,5-dienone Compound 11

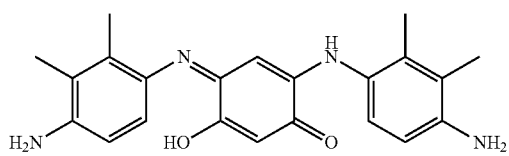

2-(4-Amino-2,3-dimethyl-phenylamino)-4-[4-amino-2,3-dimethylphenylimino]-5-hydroxy-3-methylcyclohexa-2,5-dienone Compound 12

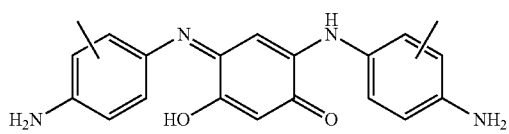

2-(4-Amino-3-methyl-phenylamino)-4-[4-amino-3 (or 2)-methyl-phenylimino]-5-hydroxycyclohexa-2,5-dienone Compound 13

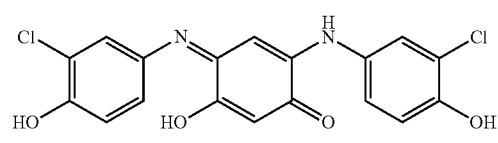

2-(3-Chloro-4-hydroxy-phenylamino)-4-[3-chloro-4-hydroxy-phenylimino]-5-hydroxy-cyclohexa-2,5-dienone Compound 14

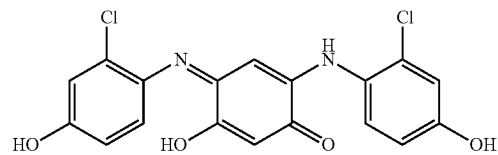

2-(2-Chloro-4-hydroxy-phenylamino)-4-[2-chloro-4-hydroxy-phenylimino]-5-hydroxy-cyclohexa-2,5-dienone Compound 15

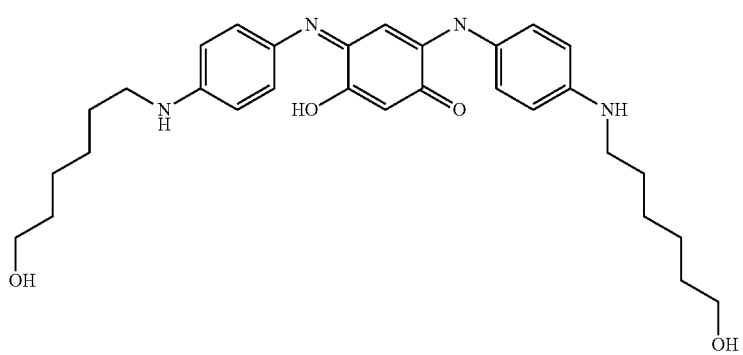

5-Hydroxy-2-[4-(6-hydroxy-hexylamino)phenylamino]-4-[4-(6-hydroxy-hexylamino)phenylimino]-cyclohexa-2,5-dienone Compound 16

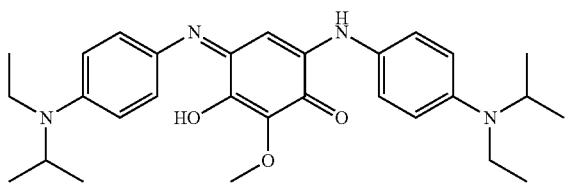

6-[4-(Ethylisopropylamino)-phenyl-amino]-4-[4-(ethylisopropyl-amino)phenylimino]-3-hydroxy-2-methoxycyclohexa-2,5-dienone Compound 17

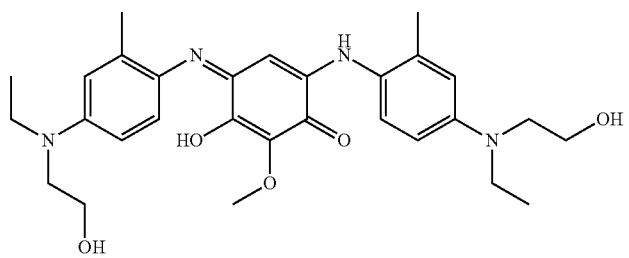

2-{4-[Ethyl(2-hydroxyethyl)-amino]-2-methyl-phenylamino}-4-{4-[ethyl(2-hydroxyethyl)amino]-2-methylphenylimino}-2-hydroxy-2-methoxy-cyclohexa-2,5-dienone Compound 18

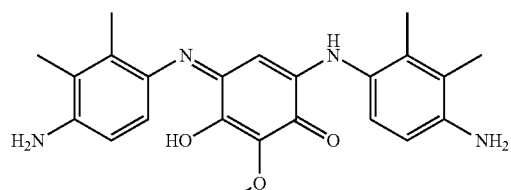

2-(4-Amino-2,3-dimethyl-phenylamino)-4-[4-amino-2,3-dimethylphenylimino]-3-hydroxy-2-methoxycyclohexa-2,5-dienone Compound 19

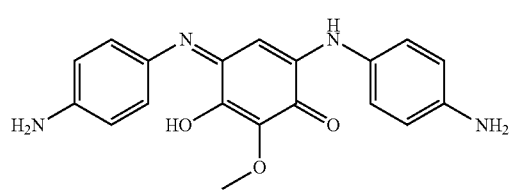

2-(4-Aminophenylamino)-4-[4-aminophenylimino]-3-hydroxy-2-methoxy-cyclohexa-2,5-dienone Compound 20

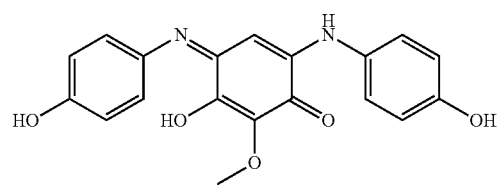

3-Hydroxy-2-(4-hydroxy-phenylamino)-4-[4-hydroxyphenylimino]-2-methoxycyclohexa-2,5-dienone Compound 21

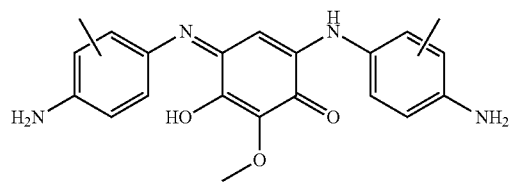

2-(4-Amino-3 (or 2)-methyl-phenylamino)-4-[4-amino-3 (or 2)-methyl-phenylimino]-3-hydroxy-2-methoxycyclohexa-2,5-dienone Compound 22

-continued

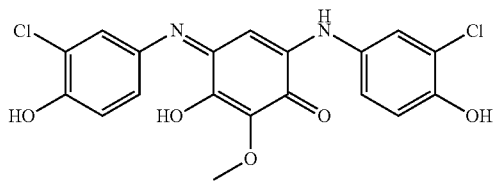

Compound 23

2-(3-Chloro-4-hydroxy-
phenylamino)-
4-[3-chloro-4-hydroxy-
phenylimino]-3-hydroxy-2-
methoxycyclohexa-2,5-dienone

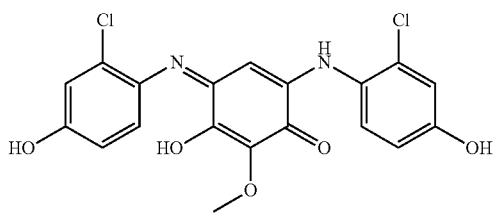

Compound 24

2-(2-Chloro-4-hydroxy-
phenylamino)-
4-[2-chloro-4-hydroxy-
phenylimino]-3-hydroxy-2-
methoxycyclohexa-2,5-
dienone

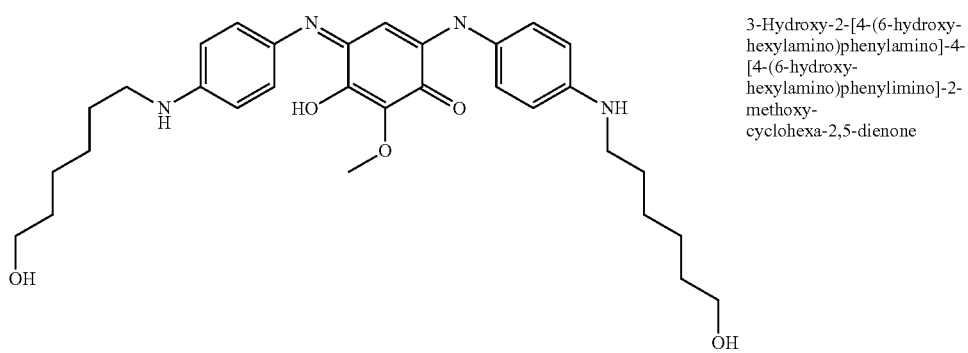

Compound 25

3-Hydroxy-2-[4-(6-hydroxy-
hexylamino)phenylamino]-4-
[4-(6-hydroxy-
hexylamino)phenylimino]-2-
methoxy-
cyclohexa-2,5-dienone

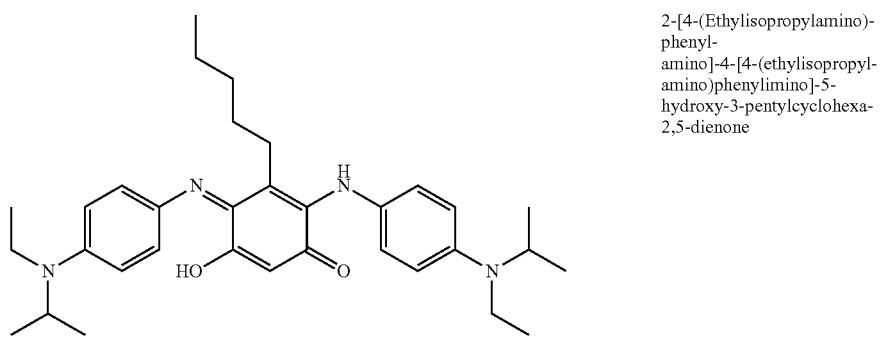

Compound 26

2-[4-(Ethylisopropylamino)-
phenyl-
amino]-4-[4-(ethylisopropyl-
amino)phenylimino]-5-
hydroxy-3-pentylcyclohexa-
2,5-dienone

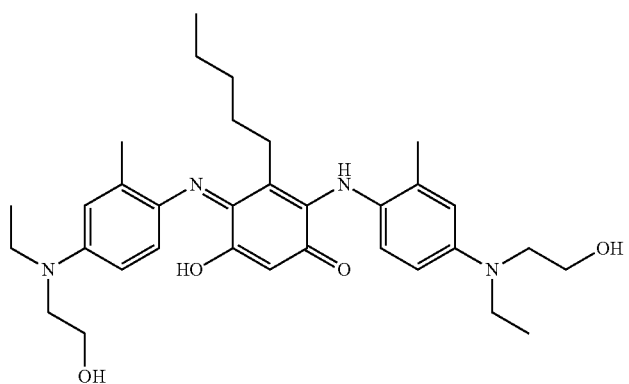

2-{4-[Ethyl(2-hydroxyethyl)-amino]-2-methyl-phenylamino}-4-{4-[ethyl(2-hydroxyethyl)amino]-2-methylphenylimino}-5-hydroxy-3-pentyl-cyclohexa-2,5-dienone Compound 27

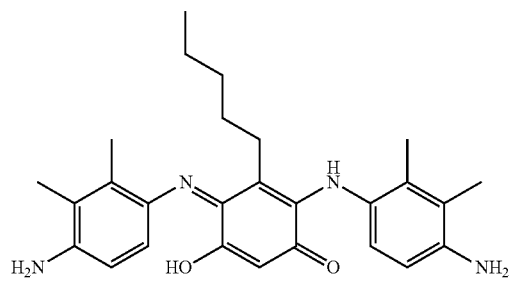

2-(4-Amino-2,3-dimethyl-phenylamino)-4-[4-amino-2,3-dimethylphenylimino]-5-hydroxy-3-pentylcyclohexa-2,5-dienone Compound 28

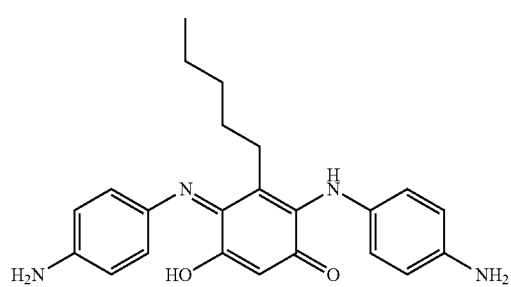

2-(4-Aminophenylamino)-4-[4-aminophenylimino]-5-hydroxy-3-pentyl-cyclohexa-2,5-dienone Compound 29

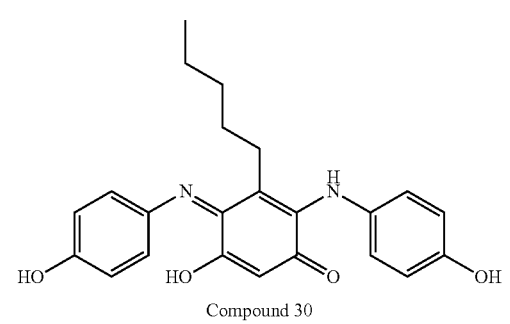 [SMILES: CCCCCC1=C(Nc2ccc(O)cc2)C(=O)C=C(O)/C1=N\c1ccc(O)cc1]

5-Hydroxy-2-(4-hydroxy-phenylamino)-4-[4-hydroxyphenylimino]-3-pentylcyclohexa-2,5-dienone Compound 30

-continued

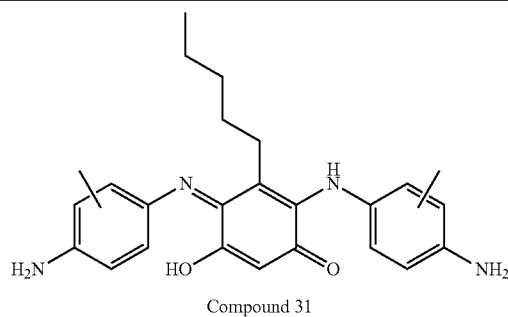

Compound 31

2-(4-Amino-3 (or 2)-methyl-phenylamino)-4-[4-amino-3 (or 2)-methyl-phenylimino]-5-hydroxy-3-pentylcyclohexa-2,5-dienone

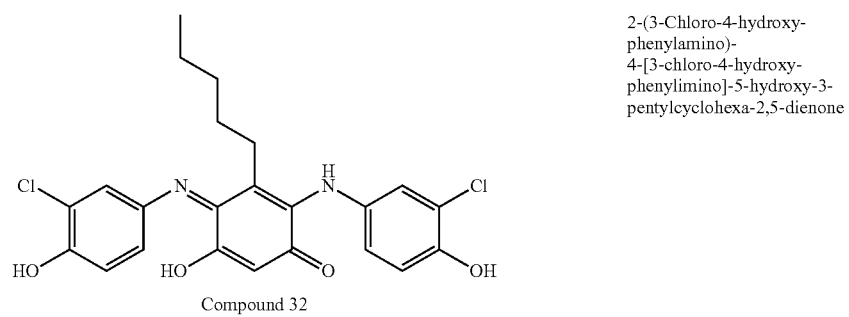

Compound 32

2-(3-Chloro-4-hydroxy-phenylamino)-4-[3-chloro-4-hydroxy-phenylimino]-5-hydroxy-3-pentylcyclohexa-2,5-dienone

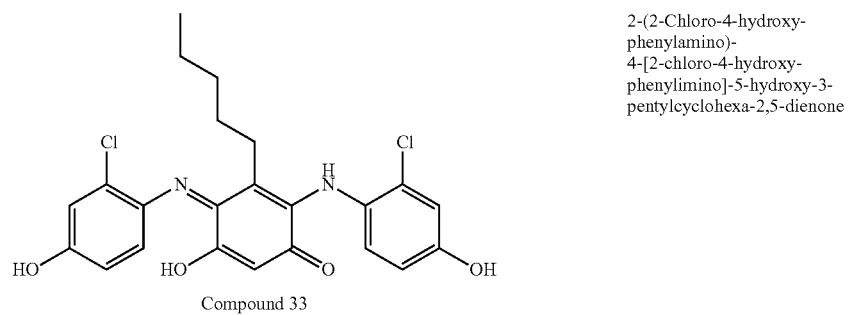

Compound 33

2-(2-Chloro-4-hydroxy-phenylamino)-4-[2-chloro-4-hydroxy-phenylimino]-5-hydroxy-3-pentylcyclohexa-2,5-dienone

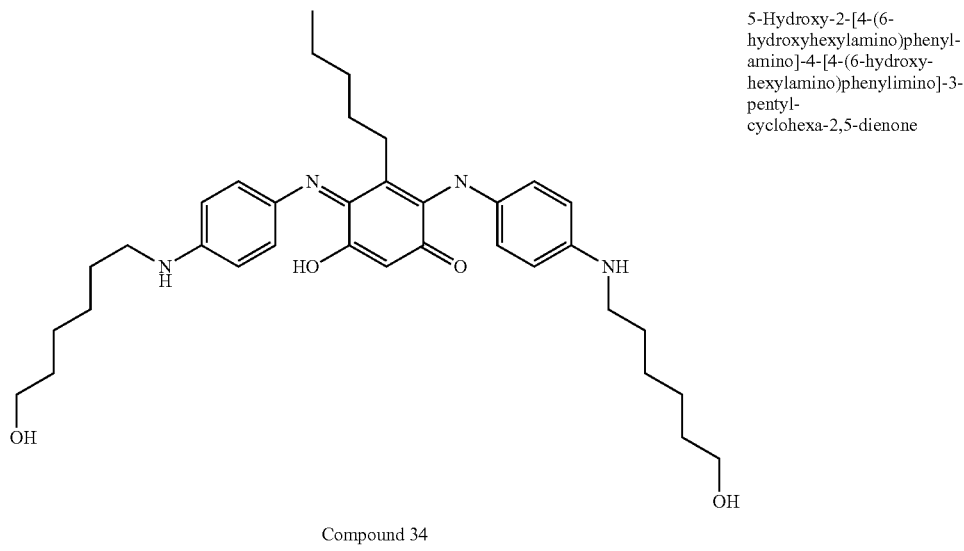

Compound 34

5-Hydroxy-2-[4-(6-hydroxyhexylamino)phenyl-amino]-4-[4-(6-hydroxy-hexylamino)phenylimino]-3-pentyl-cyclohexa-2,5-dienone

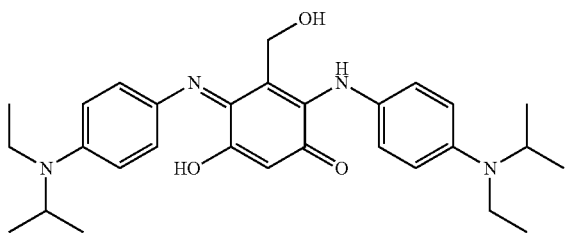

Compound 35

2-[4-(Ethylisopropylamino)-phenyl-amino]-4-[4-(ethylisopropyl-amino)phenylimino]-5-hydroxy-3-hydroxymethyl-cyclohexa-2,5-dienone

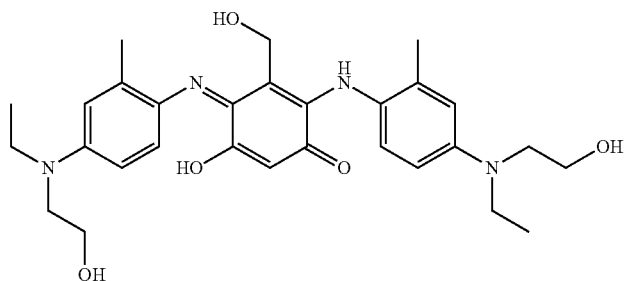

Compound 36

2-{4-[Ethyl(2-hydroxyethyl)-amino]-2-methyl-phenylamino}-4-{4-[ethyl(2-hydroxyethyl)amino]-2-methylphenylimino}-5-hydroxy-3-hydroxymethyl-cyclohexa-2,5-dienone

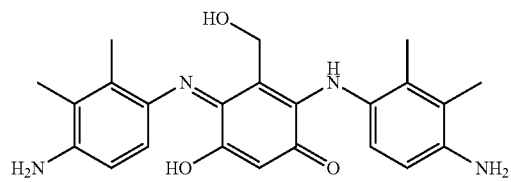

Compound 37

2-(4-Amino-2,3-dimethylphenylamino)-4-[4-amino-2,3-dimethylphenylimino]-5-hydroxy-3-hydroxymethyl-cyclohexa-2,5-dienone

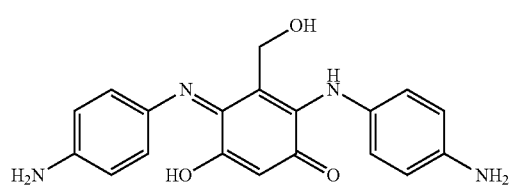

Compound 38

2-(4-Aminophenylamino)-4-[4-aminophenylimino]-5-hydroxy-3-hydroxymethyl-cyclohexa-2,5-dienone

Compound 39

5-Hydroxy-2-(4-hydroxy-phenylamino)-4-[4-hydroxyphenylimino]-3-hydroxymethylcyclohexa-2,5-dienone

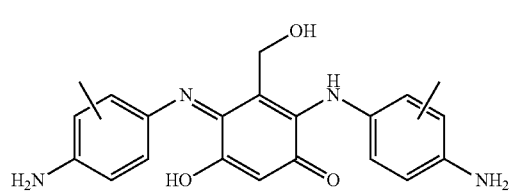

Compound 40

2-(4-Amino-3 (or 2)-methyl-phenylamino)-4-[4-amino-3 (or 2)-methyl-phenylimino]-5-hydroxy-3-hydroxymethyl-cyclohexa-2,5-dienone -continued

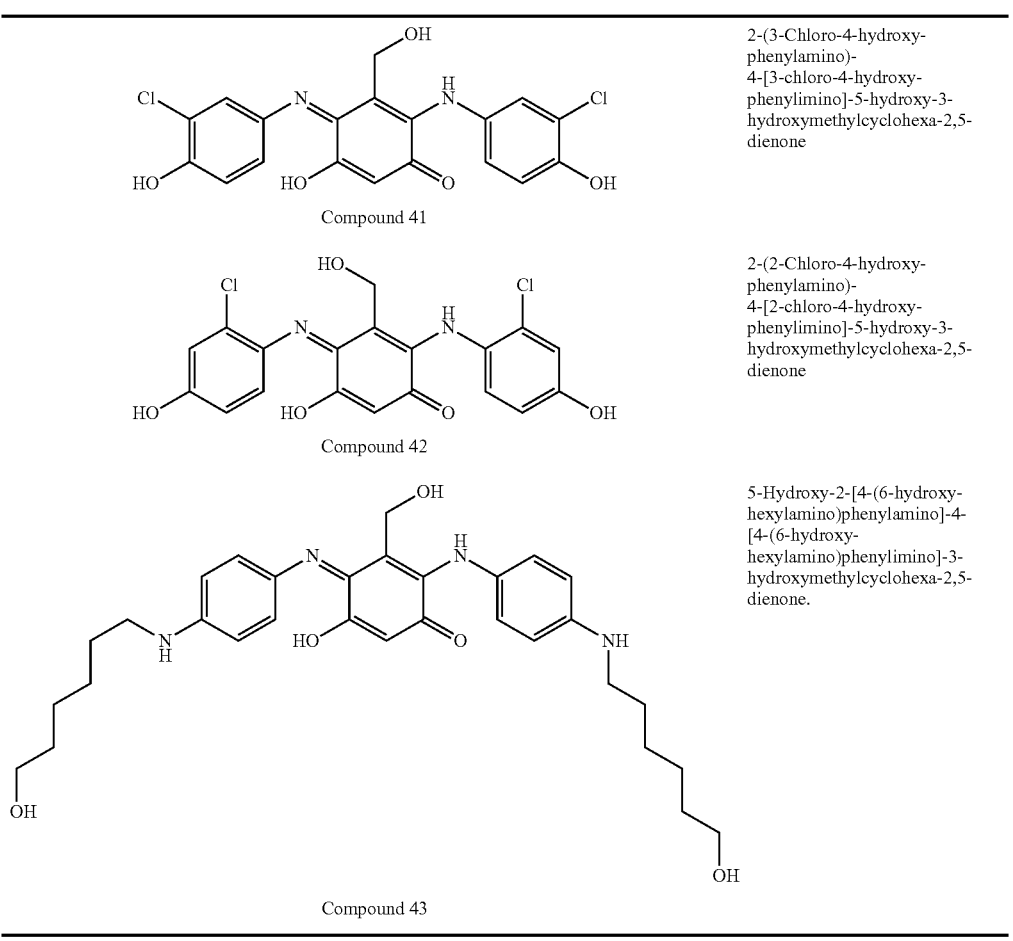

| | |
|---|---|
| Compound 41 | 2-(3-Chloro-4-hydroxy-phenylamino)-4-[3-chloro-4-hydroxy-phenylimino]-5-hydroxy-3-hydroxymethylcyclohexa-2,5-dienone |
| Compound 42 | 2-(2-Chloro-4-hydroxy-phenylamino)-4-[2-chloro-4-hydroxy-phenylimino]-5-hydroxy-3-hydroxymethylcyclohexa-2,5-dienone |
| Compound 43 | 5-Hydroxy-2-[4-(6-hydroxy-hexylamino)phenylamino]-4-[4-(6-hydroxy-hexylamino)phenylimino]-3-hydroxymethylcyclohexa-2,5-dienone. |

7. A composition for dyeing keratin fibers, comprising, in a suitable dyeing medium, at least one azomethine-type direct dye of formula (I):

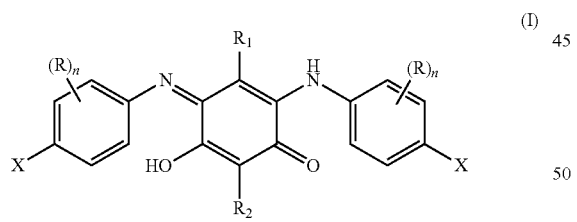

wherein:
  n is an integer equal to 0, 1, 2, 3 or 4;
  R is chosen from:
    a linear or branched $C_1$-$C_4$ alkyl radical,
    a linear or branched $C_1$-$C_4$ alkyl radical substituted with at least one radical chosen from hydroxyl, imidazolium, and $An^-$ radicals, wherein $An^-$ represents a cosmetically acceptable anion or a combination of anions,
    a $C_1$-$C_4$ alkoxy radical, and
    a halogen atom;
  $R_1$ is chosen from:
    a hydrogen atom,
    a linear or branched $C_1$-$C_9$ alkyl radical,
    a linear or branched $C_1$-$C_9$ alkyl radical substituted with at least one hydroxyl radical, and
    a $C_1$-$C_3$ alkoxy radical;
  $R_2$ is chosen from:
    a hydrogen atom, and
    a $C_1$-$C_3$ alkoxy radical;
  X is chosen from:
    a hydroxyl radical, and
    a —$NR_3R_4$ radical wherein $R_3$ is chosen from a hydrogen atom, or a linear or branched $C_1$-$C_6$ alkyl radical, and $R_4$, which may be identical or different, is chosen from a hydrogen atom, a linear or branched $C_1$-$C_6$ alkyl radical, or a linear or branched $C_1$-$C_6$ alkyl radical substituted with at least one hydroxyl or $C_1$-$C_4$ alkoxy radical;
  when $R_1$ and $R_2$ represent a hydrogen atom and n equals 0 then X does not represent a hydroxyl or amino —$NH_2$ radical.

8. A method for dyeing keratin fibers, the method comprising:
  applying to the keratin fibers a dye composition comprising, in a suitable medium for dyeing, for a time sufficient to obtain a desired coloration, at least one azomethine-type direct dye of formula (I):

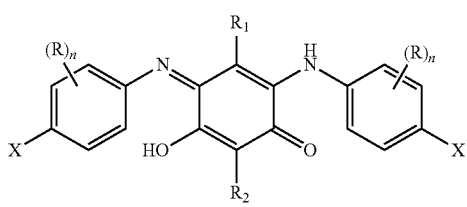

(I)

wherein:
n is an integer equal to 0, 1, 2, 3 or 4;
R is chosen from:
  a linear or branched $C_1$-$C_4$ alkyl radical,
  a linear or branched $C_1$-$C_4$ alkyl radical substituted with at least one radical chosen from hydroxyl, imidazolium, and $An^-$ radicals, wherein $An^-$ represents a cosmetically acceptable anion or a combination of anions,
  a $C_1$-$C_4$ alkoxy radical, and
  a halogen atom;
$R_1$ is chosen from:
  a hydrogen atom,
  a linear or branched $C_1$-$C_9$ alkyl radical,
  a linear or branched $C_1$-$C_9$ alkyl radical substituted with at least one hydroxyl radical, and
  a $C_1$-$C_3$ alkoxy radical;
$R_2$ is chosen from:
  a hydrogen atom, and
  a $C_1$-$C_3$ alkoxy radical;
X is chosen from:
  a hydroxyl radical, and
  a —$NR_3R_4$ radical wherein $R_3$ is chosen from a hydrogen atom or a linear or branched 1 radical, and $R_4$, which may be identical or different, is chosen from a hydrogen atom, a linear or branched $C_1$-$C_6$ alkyl radical, or a linear or branched $C_1$-$C_6$ alkyl radical substituted with at least one hydroxyl or $C_1$-$C_4$ alkoxy radical;
when $R_1$ and $R_2$ represent a hydrogen atom and n equals 0 then X does not represent a hydroxyl or amino —$NH_2$ radical;
rinsing the fibers;
optionally washing the fibers with shampoo;
optionally rinsing the fibers; and
drying the keratin fibers or leaving the keratin fibers to dry.

9. A method for lightening keratin fibers, the method comprising:
applying a dye composition comprising, in a suitable dyeing medium, (i) at least one azomethine-type direct dye of formula (I) free of oxidizing agent, and (ii) a cosmetic composition comprising at least one oxidizing agent, wherein compositions (i) and (ii) are applied to the keratin fibers sequentially or simultaneously for a time sufficient to obtain a desired lightening:

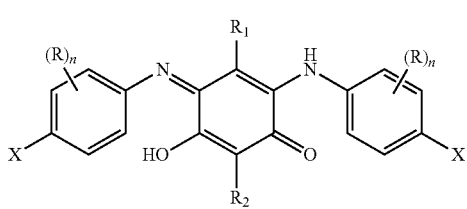

(I)

wherein:
n is an integer equal to 0, 1, 2, 3 or 4;
R is chosen from:
  a linear or branched $C_1$-$C_4$ alkyl radical,
  a linear or branched $C_1$-$C_4$ alkyl radical substituted with at least one radical chosen from hydroxyl, imidazolium, and $An^-$ radicals, wherein $An^-$ represents a cosmetically acceptable anion or a combination of anions,
  a $C_1$-$C_4$ alkoxy radical, and
  a halogen atom;
$R_1$ is chosen from:
  a hydrogen atom,
  a linear or branched $C_1$-$C_9$ alkyl radical,
  a linear or branched $C_1$-$C_9$ alkyl radical substituted with at least one hydroxyl radical, and
  a $C_1$-$C_3$ alkoxy radical;
$R_2$ is chosen from:
  a hydrogen atom, and
  a $C_1$-$C_3$ alkoxy radical;
X is chosen from:
  a hydroxyl radical, and
  a —$NR_3R_4$ radical wherein $R_3$ is chosen from a hydrogen atom or a linear or branched $C_1$-$C_6$ alkyl radical, and $R_4$, which may be identical or different, is chosen from a hydrogen atom, a linear or branched $C_1$-$C_6$ alkyl radical, or a linear or branched $C_1$-$C_6$ alkyl radical substituted with at least one hydroxyl or $C_1$-$C_4$ alkoxy radical;
when $R_1$ and $R_2$ represent a hydrogen atom and n equals 0 then X does not represent a hydroxyl or amino —$NH_2$ radical;
rinsing the fibers;
optionally washing the fibers with shampoo;
optionally rinsing the fibers; and
drying the fibers or leaving the fibers to dry.

10. A leuco-type compound having the following formula (II), the organic or inorganic salts with an acid or a base thereof, the tautomeric forms thereof, the optical isomers and geometric isomers thereof, and the solvates thereof:

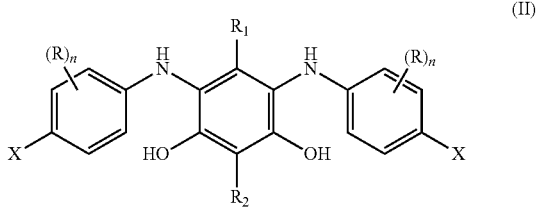

(II)

wherein:
  wherein:
    n is an integer equal to 0, 1, 2, 3 or 4;
    R is chosen from:
      a linear or branched $C_1$-$C_4$ alkyl radical,
      a linear or branched $C_1$-$C_4$ alkyl radical substituted with at least one radical chosen from hydroxyl, imidazolium, and $An^-$ radicals, wherein $An^-$ represents a cosmetically acceptable anion or a combination of anions,
      a $C_1$-$C_4$ alkoxy radical, and
      a halogen atom;
    $R_1$ is chosen from:
      a hydrogen atom,
      a linear or branched $C_1$-$C_9$ alkyl radical, a linear or branched $C_1$-$C_9$ alkyl radical substituted with at least one hydroxyl radical, and
a $C_1$-$C_3$ alkoxy radical;
$R_2$ is chosen from:
a hydrogen atom, and
a $C_1$-$C_3$ alkoxy radical;
X is chosen from:
a hydroxyl radical, and
a —$NR_3R_4$ radical wherein $R_3$ is chosen from a hydrogen atom or a linear or branched $C_1$-$C_6$ alkyl radical, and $R_4$, which may be identical or different, is chosen from a hydrogen atom, a linear or branched $C_1$-$C_6$ alkyl radical, or a linear or branched $C_1$-$C_6$ alkyl radical substituted with at least one hydroxyl or $C_1$-$C_4$ alkoxy radical;
when $R_1$ and $R_2$ represent a hydrogen atom and n equals 0 then X does not represent a hydroxyl or amino —$NH_2$ radical.

11. A cosmetic composition comprising, in a cosmetically acceptable medium, at least one leuco-type compound of formula (II) as defined according to claim 10.

12. A method for dyeing keratin fibers, the method comprising:
applying to the fibers for a time sufficient to develop a desired coloration, a cosmetic composition comprising at least one leuco-type compound of formula (II) in the presence of at least one oxidizing agent:

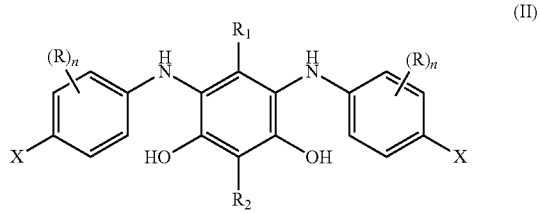

(II)

wherein:
n is an integer equal to 0, 1, 2, 3 or 4;
R is chosen from:
a linear or branched $C_1$-$C_4$ alkyl radical,
a linear or branched $C_1$-$C_4$ alkyl radical substituted with at least one radical chosen from hydroxyl, imidazolium, and $An^-$ radicals, wherein $An^-$ represents a cosmetically acceptable anion or a combination of anions,
a $C_1$-$C_4$ alkoxy radical, and
a halogen atom;
$R_1$ is chosen from:
a hydrogen atom,
a linear or branched $C_1$-$C_9$ alkyl radical,
a linear or branched $C_1$-$C_9$ alkyl radical substituted with at least one hydroxyl radical, and
a $C_1$-$C_3$ alkoxy radical;
$R_2$ is chosen from:
a hydrogen atom, and
a $C_1$-$C_3$ alkoxy radical;
X is chosen from:
a hydroxyl radical, and
a —$NR_3R_4$ radical wherein $R_3$ is chosen from a hydrogen atom or a linear or branched $C_1$-$C_6$ alkyl radical, and $R_4$, which may be identical or different, is chosen from a hydrogen atom, a linear or branched $C_1$-$C_6$ alkyl radical, or a linear or branched $C_1$-$C_6$ alkyl radical substituted with at least one hydroxyl or $C_1$-$C_4$ alkoxy radical;
when $R_1$ and $R_2$ represent a hydrogen atom and n equals 0 then X does not represent a hydroxyl or amino —$NH_2$ radical;
rinsing the fibers;
optionally washing the fibers with shampoo;
optionally rinsing the fibers, and
drying the fibers or leaving the fibers to dry.

13. A multi-compartment device comprising a first compartment configured to contain the dye composition according to claim 7, and a second compartment configured to contain at least one oxidizing agent.

14. A multi-compartment kit comprising a first compartment configured to contain the dye composition according to claim 7, and a second compartment configured to contain at least one oxidizing agent.

15. A multi-compartment device comprising a first compartment configured to contain the dye composition according to claim 10, and a second compartment configured to contain at least one oxidizing agent.

16. A multi-compartment kit comprising a first compartment configured to contain the dye composition according to claim 10, and a second compartment configured to contain at least one oxidizing agent.

* * * * *

UNITED STATES PATENT AND TRADEMARK OFFICE
CERTIFICATE OF CORRECTION

PATENT NO. : 9,439,844 B2
APPLICATION NO. : 14/365228
DATED : September 13, 2016
INVENTOR(S) : Stephane Sabelle et al.

Page 1 of 1

It is certified that error appears in the above-identified patent and that said Letters Patent is hereby corrected as shown below:

Title page, (72) Inventors: please change "Madeline" to -- Madeleine --; and

In the Claims

Col. 59, line 34, please change "1" to -- C1-C6 alkyl --.

Signed and Sealed this
First Day of November, 2016

Michelle K. Lee
*Director of the United States Patent and Trademark Office*